(12) United States Patent
Bao et al.

(10) Patent No.: US 7,592,505 B2
(45) Date of Patent: Sep. 22, 2009

(54) UDP-XYLOSE SYNTHASES (UXS) POLYNUCLEOTIDES, POLYPEPTIDES, AND USES THEREOF

(75) Inventors: Xiaoming Bao, Johnston, IA (US); George W. Singletary, Ankeny, IA (US); Deborah J. Wetterberg, Des Moines, IA (US); Ramesh Nair, Ankeny, IA (US); Kanwarpal S. Dhugga, Johnston, IA (US); Matthias Liebergesell, Kennett Square, PA (US); David A. Selinger, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 117 days.

(21) Appl. No.: 11/614,098

(22) Filed: Dec. 21, 2006

(65) Prior Publication Data

US 2007/0199105 A1    Aug. 23, 2007

Related U.S. Application Data

(60) Provisional application No. 60/755,253, filed on Dec. 30, 2005.

(51) Int. Cl.
| | |
|---|---|
| *C12N 15/82* | (2006.01) |
| *C12N 15/63* | (2006.01) |
| *C12N 15/52* | (2006.01) |
| *C12N 15/11* | (2006.01) |
| *A01H 5/00* | (2006.01) |

(52) U.S. Cl. .................. 800/285; 800/286; 800/295; 800/298; 435/320.1; 435/468; 536/23.1; 536/23.2; 536/23.6; 536/24.5

(58) Field of Classification Search ................ None
See application file for complete search history.

(56) References Cited

U.S. PATENT DOCUMENTS

2004/0034888 A1* 2/2004 Liu et al. ................... 800/289

OTHER PUBLICATIONS

York et al 2008 Current Opinion in Plant Biology 11:258-265.*
Hayashi, et al., Formation of UDP-Xylose and Xyloglucan in Soybean Golgi Membranes, Plant Physiol. (1988), 87:341-345.
Reiter, et al., Molecular genetics of nucleotide sugar interconversion pathways in plants, Plant Mol. Biol. (2001), 47:95-113.
Bar-Peled, et al., Functional cloning and characterization of a UDP-glucuronic acid decarboxylase: The pathogenic fungus *Cryptococcus neoformans* elucidates UDP-xylose synthesis, PNAS (2001), 98(21):12003-12008.
Moriarity, et al., UDP-glucuronate Decarboxylase, a Key Enzyme in Proteoglycan Synthesis, J. of Biol. Chem. (2002), 277(19):16968-16975.
Kobayashi, et al., Purification and cDNA Cloning of UDP-D-Glucuronate Carboxy-lase (UDP-D-xylose Synthase) from Pea Seedlings, Plant Cell Phys. (2002), 43(11):1259-1265.
Wheatley, et al., Characterisation and immunolocation of an 87 kDa polypeptide associated with UDP-glucuronic acid decarboxylase activity from differentiating tobacco cells (*Nicotiana tabacum* L.), Phytochem. (2002), 61:771-780.
Harper, et al., Biosynthesis of UDP-Xylose. Cloning and Characterization of a Novel *Arabidopsis* Gene Family, UXS, Encoding Soluble and Putative Membrane-Bound UDP-Glucuronic Acid Decarboxylase isoforms, Plant Phys. (2002), 130:2188-2198.
Pagny, et al., Structural requirements for *Arabidopsis* B1,2-xylosyltransferase activity and targeting to the Golgi, Plant J. (2003), 33:189-203.
Suzuki, et al., Cloning and expression of a UDP-glucuronic acid decarboxylase gene in rice, J. of Experimental Botany, (2003) 54(389):1997-1999.
Seifert, Georg J, Nucleotide sugar interconversions and cell wall biosynthesis: how to bring the inside to the outside, Science Direct (2004), 7:277-284.
Gu, et al., The Biosynthesis of UDP-Galacturonic Acid in Plants. Functional Cloning and Characterization of Arabidopsis UDP-D-Glucuronic Acid 4-Epimerase, Plant Phys. (2004), 136:4256-4264.
Pattathil, et al., Biosynthesis of UDP-xylose: characterization of membrane-bound At Uxs2, Planta (2005), 221:538-538.
Gardiner, et al., Zea mays PC0092342 mRNA sequence, NCBI Accession No. AY104952 (2005).

* cited by examiner

*Primary Examiner*—Anne Marie Grunberg
*Assistant Examiner*—Brent Page
(74) *Attorney, Agent, or Firm*—Kathryn K. Lappegard; Pioneer Hi-Bred International, Inc.

(57) ABSTRACT

The present disclosure concerns methods and compositions relating to UXS polypeptides and/or nucleic acids encoding UXS polypeptides. In certain claims, the methods and compositions are of use to improve digestibility and/or ease of grain processing. Such improvements relate to a modulation in arabinoxylan and/or hemicellulose content in transgenic plants. Such plants can, for example, comprise one or more nucleic acid sequences that inhibit expression of one or more UDP-Xylose Synthase (UXS) genes.

10 Claims, No Drawings

```
                              SEQUENCE LISTING

<160> NUMBER OF SEQ ID NOS: 19

<210> SEQ ID NO 1
<211> LENGTH: 1436
<212> TYPE: DNA
<213> ORGANISM: Zea mays
<220> FEATURE:
<221> NAME/KEY: CDS
<222> LOCATION: (88)...(1140)
<223> OTHER INFORMATION: ZmUXS1

<400> SEQUENCE: 1
ttcaaacccg cccgttcccc gtgtccgagc cacgcaagcc gagctcaatc cccagaggcc         60
agagccagct gctcggcgct ccacgcg atg gcg cag aag gag acc aat ggc agc        114
                              Met Ala Gln Lys Glu Thr Asn Gly Ser
                                1               5 aac ggc gag cac atc tcc acc cgc ccg ccg acc ccg tcg ccc ctc             162
Asn Gly Glu His Ile Ser Thr Arg Pro Pro Thr Pro Ser Pro Leu
 10              15                  20                  25 cgc ttc tcc aag ttc ttc cag gct aac ctg cgg atc ctg gtc act ggt         210
Arg Phe Ser Lys Phe Phe Gln Ala Asn Leu Arg Ile Leu Val Thr Gly
                 30                  35                  40 ggg gcg ggc ttc atc ggc tcg cac ctc gtg gac agg ctc atg gag aac         258
Gly Ala Gly Phe Ile Gly Ser His Leu Val Asp Arg Leu Met Glu Asn
             45                  50                  55 gag aag cac gag gtc att gtt gct gat aac ttt ttc acc ggt tca aaa         306
Glu Lys His Glu Val Ile Val Ala Asp Asn Phe Phe Thr Gly Ser Lys
         60                  65                  70 gat aac ctg aag aag tgg atc gga cac cca aga ttt gag ctc atc cgc         354
Asp Asn Leu Lys Lys Trp Ile Gly His Pro Arg Phe Glu Leu Ile Arg
     75                  80                  85 cat gat gtc act gag cca ctt ctt gtg gag gtt gac cag atc tat cac         402
His Asp Val Thr Glu Pro Leu Leu Val Glu Val Asp Gln Ile Tyr His
 90                  95                 100                 105 ctt gct tgc cct gct tca cca atc ttc tac aag cac aat cct gtt aag         450
Leu Ala Cys Pro Ala Ser Pro Ile Phe Tyr Lys His Asn Pro Val Lys
                110                 115                 120 acc atc aag aca aat gtt att ggt acc ctg aac atg ctg gga ctt gca         498
Thr Ile Lys Thr Asn Val Ile Gly Thr Leu Asn Met Leu Gly Leu Ala
            125                 130                 135 aag aga gtt gga gct agg att ttg ttg aca tca aca tct gaa gtt tat         546
Lys Arg Val Gly Ala Arg Ile Leu Leu Thr Ser Thr Ser Glu Val Tyr
        140                 145                 150 ggt gat cca ctt gag cat cct caa acc gag gcc tac tgg ggc aat gtt         594
Gly Asp Pro Leu Glu His Pro Gln Thr Glu Ala Tyr Trp Gly Asn Val
    155                 160                 165 aac cca att gga gtc agg agt tgt tat gat gag ggt aag cgt gta gca         642
Asn Pro Ile Gly Val Arg Ser Cys Tyr Asp Glu Gly Lys Arg Val Ala
```

```
                170                 175                 180                 185
gag acg ctg atg ttc gac tat cac agg cag cat ggc att gaa atc cga       690
Glu Thr Leu Met Phe Asp Tyr His Arg Gln His Gly Ile Glu Ile Arg
                    190                 195                 200 att gcc agg att ttc aac acc tat ggg cca agg atg aac att gac gat       738
Ile Ala Arg Ile Phe Asn Thr Tyr Gly Pro Arg Met Asn Ile Asp Asp
                205                 210                 215 ggc cgt gtt gtt agc aac ttc att gct cag gct gtg cgt ggc gaa ccc       786
Gly Arg Val Val Ser Asn Phe Ile Ala Gln Ala Val Arg Gly Glu Pro
            220                 225                 230 ctt act gtc cag aag cca gga aca cag act agg agc ttc tgc tat gtc       834
Leu Thr Val Gln Lys Pro Gly Thr Gln Thr Arg Ser Phe Cys Tyr Val
        235                 240                 245 gcc gat atg gtt gat ggt ctt att agg ctg atg aac gga aac aac act       882
Ala Asp Met Val Asp Gly Leu Ile Arg Leu Met Asn Gly Asn Asn Thr
250                 255                 260                 265 gga ccg att aac ttg ggg aac cca ggt gaa ttc acc atg ctg gaa ctt       930
Gly Pro Ile Asn Leu Gly Asn Pro Gly Glu Phe Thr Met Leu Glu Leu
                270                 275                 280 gct gag aat gtg aag gag ttg att aac cca gat ata aca gtg acg atg       978
Ala Glu Asn Val Lys Glu Leu Ile Asn Pro Asp Ile Thr Val Thr Met
            285                 290                 295 acc gag aac act cct gat gat ccc cgc cag agg aag ccg gac atc acc      1026
Thr Glu Asn Thr Pro Asp Asp Pro Arg Gln Arg Lys Pro Asp Ile Thr
        300                 305                 310 aag gca aag gaa gtt cta ggg tgg gag ccc aag atc gtc ctg aag gac      1074
Lys Ala Lys Glu Val Leu Gly Trp Glu Pro Lys Ile Val Leu Lys Asp
315                 320                 325 ggc ttg gtg ctc atg gag gat gat ttc cgg gag cgc ctg gcc gtg ccc      1122
Gly Leu Val Leu Met Glu Asp Asp Phe Arg Glu Arg Leu Ala Val Pro
330                 335                 340                 345 aag aaa acc aag gcc taa actgccctgc ggtgggcgaa gaatatccac             1170
Lys Lys Thr Lys Ala *
                350 ggggagcat actcatagtt ggcttgtcat tattcgtggc cacatttcat tacggaattt     1230
gagttccaat aaacggaata taccttcttc gatcaccttg aaggattgta tcattagaat    1290
tttcatacag ggctggcctt ttgagtctct gcctacgcac gcagatgttg tggttcttgt    1350
gtttgtagcc tatatgtact ccctgagtcg attatagaaa tgtttatgcc attttgagct   1410
ttttgttgaa aaaaaaaaaa aaaaaa                                         1436

<210> SEQ ID NO 2
<211> LENGTH: 350
<212> TYPE: PRT
<213> ORGANISM: Zea mays

<400> SEQUENCE: 2

Met Ala Gln Lys Glu Thr Asn Gly Ser Asn Gly Glu His Ile Ser Thr
  1               5                  10                  15

Arg Pro Pro Thr Pro Ser Pro Leu Arg Phe Ser Lys Phe Phe Gln
                20                  25                  30

Ala Asn Leu Arg Ile Leu Val Thr Gly Gly Ala Gly Phe Ile Gly Ser
            35                  40                  45

His Leu Val Asp Arg Leu Met Glu Asn Glu Lys His Glu Val Ile Val
        50                  55                  60

Ala Asp Asn Phe Phe Thr Gly Ser Lys Asp Asn Leu Lys Lys Trp Ile
65                  70                  75                  80
```

```
Gly His Pro Arg Phe Glu Leu Ile Arg His Asp Val Thr Glu Pro Leu
                 85                  90                  95

Leu Val Glu Val Asp Gln Ile Tyr His Leu Ala Cys Pro Ala Ser Pro
            100                 105                 110

Ile Phe Tyr Lys His Asn Pro Val Lys Thr Ile Lys Thr Asn Val Ile
        115                 120                 125

Gly Thr Leu Asn Met Leu Gly Leu Ala Lys Arg Val Gly Ala Arg Ile
130                 135                 140

Leu Leu Thr Ser Thr Ser Glu Val Tyr Gly Asp Pro Leu Glu His Pro
145                 150                 155                 160

Gln Thr Glu Ala Tyr Trp Gly Asn Val Asn Pro Ile Gly Val Arg Ser
                165                 170                 175

Cys Tyr Asp Glu Gly Lys Arg Val Ala Glu Thr Leu Met Phe Asp Tyr
            180                 185                 190

His Arg Gln His Gly Ile Glu Ile Arg Ile Ala Arg Ile Phe Asn Thr
        195                 200                 205

Tyr Gly Pro Arg Met Asn Ile Asp Asp Gly Arg Val Val Ser Asn Phe
210                 215                 220

Ile Ala Gln Ala Val Arg Gly Glu Pro Leu Thr Val Gln Lys Pro Gly
225                 230                 235                 240

Thr Gln Thr Arg Ser Phe Cys Tyr Val Ala Asp Met Val Asp Gly Leu
                245                 250                 255

Ile Arg Leu Met Asn Gly Asn Asn Thr Gly Pro Ile Asn Leu Gly Asn
            260                 265                 270

Pro Gly Glu Phe Thr Met Leu Glu Leu Ala Glu Asn Val Lys Glu Leu
        275                 280                 285

Ile Asn Pro Asp Ile Thr Val Thr Met Thr Glu Asn Thr Pro Asp Asp
290                 295                 300

Pro Arg Gln Arg Lys Pro Asp Ile Thr Lys Ala Lys Glu Val Leu Gly
305                 310                 315                 320

Trp Glu Pro Lys Ile Val Leu Lys Asp Gly Leu Val Leu Met Glu Asp
                325                 330                 335

Asp Phe Arg Glu Arg Leu Ala Val Pro Lys Lys Thr Lys Ala
            340                 345                 350

<210> SEQ ID NO 3
<211> LENGTH: 1537
<212> TYPE: DNA
<213> ORGANISM: Zea mays
<220> FEATURE:
<221> NAME/KEY: CDS
<222> LOCATION: (146)...(1198)
<223> OTHER INFORMATION: ZmUXS2

<400> SEQUENCE: 3
gcgcgctcta taaatacgac tcagatctga gaggccttct cctcgtccgc cccagtctaa      60
tccgattcaa accgcccgtt ccccgtgtcc gtgccaagca agccgagccc aaccccccaag    120 agccagctgc tcggtgctcc acgcg atg gcg cag aag gag act aat ggc agc      172
                              Met Ala Gln Lys Glu Thr Asn Gly Ser
                                1               5 aac ggc gat cac atc tcc acc cgc ccg ccg ccg acc ccc tcg ccc ctc      220
Asn Gly Asp His Ile Ser Thr Arg Pro Pro Pro Thr Pro Ser Pro Leu
 10                  15                  20                  25 cgc ttc tcc aag ttc ttt cag gct aac ctg cgg atc ctg gtc act ggt      268
Arg Phe Ser Lys Phe Phe Gln Ala Asn Leu Arg Ile Leu Val Thr Gly
                 30                  35                  40
```

| | | |
|---|---|---|
| ggg gcg ggc ttc atc ggc tcg cac ctc gta gac aag ctc atg gag aac<br>Gly Ala Gly Phe Ile Gly Ser His Leu Val Asp Lys Leu Met Glu Asn<br>45 50 55 | | 316 |
| gag aag cac gag gtc att gtt gct gat aac ttt ttc act ggt tca aaa<br>Glu Lys His Glu Val Ile Val Ala Asp Asn Phe Phe Thr Gly Ser Lys<br>60 65 70 | | 364 |
| gac aac ctg aag aag tgg att ggc cac cca aga ttt gag ctc atc cgt<br>Asp Asn Leu Lys Lys Trp Ile Gly His Pro Arg Phe Glu Leu Ile Arg<br>75 80 85 | | 412 |
| cat gat gtc acc gag ccg ctt ctt gtg gaa gtt gac caa atc tat cac<br>His Asp Val Thr Glu Pro Leu Leu Val Glu Val Asp Gln Ile Tyr His<br>90 95 100 105 | | 460 |
| ctt gct tgc cct gct tca cca atc ttc tac aag cac aac cct gtt aag<br>Leu Ala Cys Pro Ala Ser Pro Ile Phe Tyr Lys His Asn Pro Val Lys<br>110 115 120 | | 508 |
| acc atc aag aca aat gtt att ggt acc ctg aac atg cta gga ctt gca<br>Thr Ile Lys Thr Asn Val Ile Gly Thr Leu Asn Met Leu Gly Leu Ala<br>125 130 135 | | 556 |
| aag aga gtt gga gct agg att ttg ttg aca tca acc tct gaa gtt tat<br>Lys Arg Val Gly Ala Arg Ile Leu Leu Thr Ser Thr Ser Glu Val Tyr<br>140 145 150 | | 604 |
| ggt gat cca ctt gag cat cct caa act gag gcc tac tgg ggc aat gtt<br>Gly Asp Pro Leu Glu His Pro Gln Thr Glu Ala Tyr Trp Gly Asn Val<br>155 160 165 | | 652 |
| aac ccg att ggt gtt agg agt tgt tat gat gag ggt aag cgt gta gca<br>Asn Pro Ile Gly Val Arg Ser Cys Tyr Asp Glu Gly Lys Arg Val Ala<br>170 175 180 185 | | 700 |
| gag aca ttg atg ttc gac tat cac agg cag cat ggc att gaa atc cgg<br>Glu Thr Leu Met Phe Asp Tyr His Arg Gln His Gly Ile Glu Ile Arg<br>190 195 200 | | 748 |
| att gcc agg att ttc aac acc tac ggg cct agg atg aac att gat gat<br>Ile Ala Arg Ile Phe Asn Thr Tyr Gly Pro Arg Met Asn Ile Asp Asp<br>205 210 215 | | 796 |
| ggc cgt gtt gtt agc aac ttc att gct cag gct gtg cgc ggt gag ccc<br>Gly Arg Val Val Ser Asn Phe Ile Ala Gln Ala Val Arg Gly Glu Pro<br>220 225 230 | | 844 |
| ctg act gtc cag agg cca gga aca cag act agg agt ttc tgc tat gtt<br>Leu Thr Val Gln Arg Pro Gly Thr Gln Thr Arg Ser Phe Cys Tyr Val<br>235 240 245 | | 892 |
| gcc gat atg gtt gat ggt ctt att aag ctg atg aat gga aac agc act<br>Ala Asp Met Val Asp Gly Leu Ile Lys Leu Met Asn Gly Asn Ser Thr<br>250 255 260 265 | | 940 |
| gga ccg att aac ttg ggg aac cca ggt gaa ttc acc atg ctg gaa ctt<br>Gly Pro Ile Asn Leu Gly Asn Pro Gly Glu Phe Thr Met Leu Glu Leu<br>270 275 280 | | 988 |
| gct gag aat gtg aag gag ttg atc aac cca gat gtg aca gtg acg atg<br>Ala Glu Asn Val Lys Glu Leu Ile Asn Pro Asp Val Thr Val Thr Met<br>285 290 295 | | 1036 |
| acc gag aac act cct gat gac ccc cgc cag agg aag ccg gac atc aca<br>Thr Glu Asn Thr Pro Asp Asp Pro Arg Gln Arg Lys Pro Asp Ile Thr<br>300 305 310 | | 1084 |
| aag gcg aag gaa gtt ctg gga tgg gag ccc aag atc gtc ctg cgg gac<br>Lys Ala Lys Glu Val Leu Gly Trp Glu Pro Lys Ile Val Leu Arg Asp<br>315 320 325 | | 1132 |
| ggc ttg gtg ctc atg gag gat gat ttc cgg gag cgc ctg acc gtg ccc<br>Gly Leu Val Leu Met Glu Asp Asp Phe Arg Glu Arg Leu Thr Val Pro<br>330 335 340 345 | | 1180 |
| aag aaa acc aag gcc tga attgccctgc agttggggaa gaatatccac<br>Lys Lys Thr Lys Ala *<br>350 | | 1228 |

```
acgggggagc atactcatag tcgggctcgt cattatttgt ggccacattt cattacggaa    1288
tttgagttcc aataaactta atattccttt gtcgttcacc ttgaaggatt gtattgttag    1348
aattttcaac agggctggcc gttcgagtct ctgcctacgc agatcttgtg gtacttgtgt    1408
ttgtagccaa tgtgtgagta aaagtcgatt atagcaatgt tgatgccatt ttgggctaaa    1468
aaaaaaaaaa aaaaaaaaaa aaaaaaaaaa aaaaaaaaaa aaaaaaaaaa aaaaaaaaaa    1528
aaaaaaaac                                                           1537
```

<210> SEQ ID NO 4
<211> LENGTH: 350
<212> TYPE: PRT
<213> ORGANISM: Zea mays

<400> SEQUENCE: 4

```
Met Ala Gln Lys Glu Thr Asn Gly Ser Asn Gly Asp His Ile Ser Thr
 1               5                  10                  15

Arg Pro Pro Thr Pro Ser Pro Leu Arg Phe Ser Lys Phe Phe Gln
            20                  25                  30

Ala Asn Leu Arg Ile Leu Val Thr Gly Gly Ala Gly Phe Ile Gly Ser
        35                  40                  45

His Leu Val Asp Lys Leu Met Glu Asn Glu Lys His Glu Val Ile Val
    50                  55                  60

Ala Asp Asn Phe Phe Thr Gly Ser Lys Asp Asn Leu Lys Lys Trp Ile
65                  70                  75                  80

Gly His Pro Arg Phe Glu Leu Ile Arg His Asp Val Thr Glu Pro Leu
                85                  90                  95

Leu Val Glu Val Asp Gln Ile Tyr His Leu Ala Cys Pro Ala Ser Pro
            100                 105                 110

Ile Phe Tyr Lys His Asn Pro Val Lys Thr Ile Lys Thr Asn Val Ile
        115                 120                 125

Gly Thr Leu Asn Met Leu Gly Leu Ala Lys Arg Val Gly Ala Arg Ile
    130                 135                 140

Leu Leu Thr Ser Thr Ser Glu Val Tyr Gly Asp Pro Leu Glu His Pro
145                 150                 155                 160

Gln Thr Glu Ala Tyr Trp Gly Asn Val Asn Pro Ile Gly Val Arg Ser
                165                 170                 175

Cys Tyr Asp Glu Gly Lys Arg Val Ala Glu Thr Leu Met Phe Asp Tyr
            180                 185                 190

His Arg Gln His Gly Ile Glu Ile Arg Ile Ala Arg Ile Phe Asn Thr
        195                 200                 205

Tyr Gly Pro Arg Met Asn Ile Asp Asp Gly Arg Val Val Ser Asn Phe
    210                 215                 220

Ile Ala Gln Ala Val Arg Gly Glu Pro Leu Thr Val Gln Arg Pro Gly
225                 230                 235                 240

Thr Gln Thr Arg Ser Phe Cys Tyr Val Ala Asp Met Val Asp Gly Leu
                245                 250                 255

Ile Lys Leu Met Asn Gly Asn Ser Thr Gly Pro Ile Asn Leu Gly Asn
            260                 265                 270

Pro Gly Glu Phe Thr Met Leu Glu Leu Ala Glu Asn Val Lys Glu Leu
        275                 280                 285

Ile Asn Pro Asp Val Thr Val Thr Met Thr Glu Asn Thr Pro Asp Asp
    290                 295                 300

Pro Arg Gln Arg Lys Pro Asp Ile Thr Lys Ala Lys Glu Val Leu Gly
```

```
                305                 310                 315                 320
        Trp Glu Pro Lys Ile Val Leu Arg Asp Gly Leu Val Leu Met Glu Asp
                        325                 330                 335

Asp Phe Arg Glu Arg Leu Thr Val Pro Lys Lys Thr Lys Ala
                        340                 345                 350

<210> SEQ ID NO 5
<211> LENGTH: 1759
<212> TYPE: DNA
<213> ORGANISM: Zea mays
<220> FEATURE:
<221> NAME/KEY: CDS
<222> LOCATION: (53)...(1270)
<223> OTHER INFORMATION: ZmUXS3

<400> SEQUENCE: 5
caccaccagg tcaccaacca cgcacgcgcc tccgcctgcc cgctctcccg cc atg aag         58
                                                          Met Lys
                                                            1 cag ctc cac aag tct tcc cct acc cac gcg cca tcg ccg gcg cac gca         106
Gln Leu His Lys Ser Ser Pro Thr His Ala Pro Ser Pro Ala His Ala
         5                  10                  15 ccg gct ccc aag gcc gcc aag acg gcg cgc cca ggt ccg cgc tcc tgg         154
Pro Ala Pro Lys Ala Ala Lys Thr Ala Arg Pro Gly Pro Arg Ser Trp
     20                  25                  30 atc ggc tac gtc ctc cgc gag cag cgc ctc ctc ttc gtc ctg ctc ggt         202
Ile Gly Tyr Val Leu Arg Glu Gln Arg Leu Leu Phe Val Leu Leu Gly
 35                  40                  45                  50 gcg ctc atc gcc tcc acc ttc ttc ctc ctc cgg ccc tac ctc tcg ctc         250
Ala Leu Ile Ala Ser Thr Phe Phe Leu Leu Arg Pro Tyr Leu Ser Leu
                 55                  60                  65 tcc ccg tct tcc cac ctc ccc gac gcc cgc ccg ctc ttc tcc ttc gcc         298
Ser Pro Ser Ser His Leu Pro Asp Ala Arg Pro Leu Phe Ser Phe Ala
             70                  75                  80 acc cgc tcc ggt gtt ccc gcc ggc ttc cgc ccg ccg cag cgc cgc gtc         346
Thr Arg Ser Gly Val Pro Ala Gly Phe Arg Pro Pro Gln Arg Arg Val
         85                  90                  95 gtc gta aca ggc ggg gca ggg ttc gtc ggc agc cac ctc gtc gac cgg         394
Val Val Thr Gly Gly Ala Gly Phe Val Gly Ser His Leu Val Asp Arg
    100                 105                 110 ctt ctg gag cag ggg gac agc gtg atc gtg gtc gac aac ttc ttc acc         442
Leu Leu Glu Gln Gly Asp Ser Val Ile Val Val Asp Asn Phe Phe Thr
115                 120                 125                 130 ggc agg aag gag aac gtc gcg cac cac ctc cgg aac ccc agg ttc gag         490
Gly Arg Lys Glu Asn Val Ala His His Leu Arg Asn Pro Arg Phe Glu
                135                 140                 145 ctg ctc cgc cac gat gta gtc gag cca atc ctc ctc gag gtg gac cgg         538
Leu Leu Arg His Asp Val Val Glu Pro Ile Leu Leu Glu Val Asp Arg
            150                 155                 160 atc tac cac ctc gcg tgc ccc gcg tcg cct gtg cac tac aag tac aac         586
Ile Tyr His Leu Ala Cys Pro Ala Ser Pro Val His Tyr Lys Tyr Asn
        165                 170                 175 cca atc aag acg atc aag aca aat gtc atg gga act ttg aat atg ttg         634
Pro Ile Lys Thr Ile Lys Thr Asn Val Met Gly Thr Leu Asn Met Leu
    180                 185                 190 ggt ctg gcg aag cga att ggt gca agg ttt ttg ttg act agc aca agt         682
Gly Leu Ala Lys Arg Ile Gly Ala Arg Phe Leu Leu Thr Ser Thr Ser
195                 200                 205                 210 gaa gtt tat ggt gat ccg ctt gag cat cca cag aag gag tca tac tgg         730
Glu Val Tyr Gly Asp Pro Leu Glu His Pro Gln Lys Glu Ser Tyr Trp
                215                 220                 225
```

```
ggg cac gtt aat cct ata ggt gtt agg agc tgt tac gat gag ggg aag      778
Gly His Val Asn Pro Ile Gly Val Arg Ser Cys Tyr Asp Glu Gly Lys
        230                 235                 240 aga aca gca gag act tta act atg gac tat cat cgt ggt ggt ggt gtt      826
Arg Thr Ala Glu Thr Leu Thr Met Asp Tyr His Arg Gly Gly Gly Val
            245                 250                 255 gag gtg cgt att gcc cgt att ttc aat aca tat ggt cct cgt atg tgc      874
Glu Val Arg Ile Ala Arg Ile Phe Asn Thr Tyr Gly Pro Arg Met Cys
    260                 265                 270 ctc gac gat ggt cgt gtg gtc agc aat ttt gtt gca cag gca ctg cga      922
Leu Asp Asp Gly Arg Val Val Ser Asn Phe Val Ala Gln Ala Leu Arg
275                 280                 285                 290 agg caa ccg atg aca gtc tat ggt gac gga aaa caa act cga agt ttc      970
Arg Gln Pro Met Thr Val Tyr Gly Asp Gly Lys Gln Thr Arg Ser Phe
                295                 300                 305 caa tat gtt gct gat ctg gtt gct gga ctg atg gct cta atg gag agt     1018
Gln Tyr Val Ala Asp Leu Val Ala Gly Leu Met Ala Leu Met Glu Ser
                    310                 315                 320 gat cat att ggt cct ttc aac ttg gga aac cca gga gag ttt acc atg     1066
Asp His Ile Gly Pro Phe Asn Leu Gly Asn Pro Gly Glu Phe Thr Met
            325                 330                 335 ttg gag cta gca cag gtt gtg aag gaa aca att gac cca atg gca acc     1114
Leu Glu Leu Ala Gln Val Val Lys Glu Thr Ile Asp Pro Met Ala Thr
340                 345                 350 att gaa ttc aaa ccc aac aca gct gat gat ccc cat atg aga aag cca     1162
Ile Glu Phe Lys Pro Asn Thr Ala Asp Asp Pro His Met Arg Lys Pro
355                 360                 365                 370 gat atc acc aag gct aag caa ctg cta cat tgg gag cca aag gtc tct     1210
Asp Ile Thr Lys Ala Lys Gln Leu Leu His Trp Glu Pro Lys Val Ser
                375                 380                 385 ctc aaa gaa ggc ctt ccg cta atg gtt caa gat ttc cgt caa agg atc     1258
Leu Lys Glu Gly Leu Pro Leu Met Val Gln Asp Phe Arg Gln Arg Ile
                    390                 395                 400 tcg gat gag taa tcaaagcaat tctttttttcc ccgaatgtgc catgcacgtg        1310
Ser Asp Glu *
        405 tttgtaatca gagcaatcgt atgatactgg tcaccggttt gattctgaac gatgctgcaa   1370 ctacagtcag gagctcttca ccaactggag gcctggagcc ctgtagtacg atgtactgtg   1430 tacacaacag actgtagaat cacgcaggcc ccatttggag tgtggggatt ccatagtatt   1490 tctacgacat agtactattt ctgtgaaata gctgaaaagt tcatgggttc gtgttggttt   1550 ttttatatat atcttggtga ggcagaacag aagcaatcaa ttgttttttt tgtgcatgtg   1610 tgaaattcct gaattgtggg tggtgagaga taggatacaa tgatgtattt caggagcttt   1670 tgtaacactt gaacattcat catgtgaaaa atgtaactga atgtgttggc caaaaaaaaa   1730 aaaaaaaaa aaaaaaaaaa aaaaaaaa                                      1759

<210> SEQ ID NO 6
<211> LENGTH: 405
<212> TYPE: PRT
<213> ORGANISM: Zea mays

<400> SEQUENCE: 6

Met Lys Gln Leu His Lys Ser Ser Pro Thr His Ala Pro Ser Pro Ala
 1               5                  10                  15

His Ala Pro Ala Pro Lys Ala Ala Lys Thr Ala Arg Pro Gly Pro Arg
            20                  25                  30
```

```
Ser Trp Ile Gly Tyr Val Leu Arg Glu Gln Arg Leu Leu Phe Val Leu
         35                  40                  45

Leu Gly Ala Leu Ile Ala Ser Thr Phe Phe Leu Leu Arg Pro Tyr Leu
 50                  55                  60

Ser Leu Ser Pro Ser Ser His Leu Pro Asp Ala Arg Pro Leu Phe Ser
 65                  70                  75                  80

Phe Ala Thr Arg Ser Gly Val Pro Ala Gly Phe Arg Pro Pro Gln Arg
                 85                  90                  95

Arg Val Val Thr Gly Gly Ala Gly Phe Val Gly Ser His Leu Val
                100                 105                 110

Asp Arg Leu Leu Glu Gln Gly Asp Ser Val Ile Val Val Asp Asn Phe
                115                 120                 125

Phe Thr Gly Arg Lys Glu Asn Val Ala His His Leu Arg Asn Pro Arg
    130                 135                 140

Phe Glu Leu Leu Arg His Asp Val Val Glu Pro Ile Leu Leu Glu Val
145                 150                 155                 160

Asp Arg Ile Tyr His Leu Ala Cys Pro Ala Ser Pro Val His Tyr Lys
                165                 170                 175

Tyr Asn Pro Ile Lys Thr Ile Lys Thr Asn Val Met Gly Thr Leu Asn
                180                 185                 190

Met Leu Gly Leu Ala Lys Arg Ile Gly Ala Arg Phe Leu Leu Thr Ser
        195                 200                 205

Thr Ser Glu Val Tyr Gly Asp Pro Leu Glu His Pro Gln Lys Glu Ser
    210                 215                 220

Tyr Trp Gly His Val Asn Pro Ile Gly Val Arg Ser Cys Tyr Asp Glu
225                 230                 235                 240

Gly Lys Arg Thr Ala Glu Thr Leu Thr Met Asp Tyr His Arg Gly Gly
                245                 250                 255

Gly Val Glu Val Arg Ile Ala Arg Ile Phe Asn Thr Tyr Gly Pro Arg
            260                 265                 270

Met Cys Leu Asp Asp Gly Arg Val Val Ser Asn Phe Val Ala Gln Ala
        275                 280                 285

Leu Arg Arg Gln Pro Met Thr Val Tyr Gly Asp Gly Lys Gln Thr Arg
    290                 295                 300

Ser Phe Gln Tyr Val Ala Asp Leu Val Ala Gly Leu Met Ala Leu Met
305                 310                 315                 320

Glu Ser Asp His Ile Gly Pro Phe Asn Leu Gly Asn Pro Gly Glu Phe
                325                 330                 335

Thr Met Leu Glu Leu Ala Gln Val Val Lys Glu Thr Ile Asp Pro Met
            340                 345                 350

Ala Thr Ile Glu Phe Lys Pro Asn Thr Ala Asp Asp Pro His Met Arg
        355                 360                 365

Lys Pro Asp Ile Thr Lys Ala Lys Gln Leu Leu His Trp Glu Pro Lys
    370                 375                 380

Val Ser Leu Lys Glu Gly Leu Pro Leu Met Val Gln Asp Phe Arg Gln
385                 390                 395                 400

Arg Ile Ser Asp Glu
                405

<210> SEQ ID NO 7
<211> LENGTH: 1704
<212> TYPE: DNA
<213> ORGANISM: Zea mays
<220> FEATURE:
<221> NAME/KEY: CDS
```

<222> LOCATION: (64)...(1281)
<223> OTHER INFORMATION: ZmUXS4

<400> SEQUENCE: 7

| | | |
|---|---|---|
| ccacgcgtcc gatcatacca ggtcaccata cccgcctccg ccgcctggcc gcgctctccc | | 60 |
| gcc atg aag cag ctc cac aag tct tcc ccc acc caa gcg cca tcg ccg<br>    Met Lys Gln Leu His Lys Ser Ser Pro Thr Gln Ala Pro Ser Pro<br>     1                  5               10             15 | | 108 |
| gcg cac gca ccg gct ccc aag gca gcc aag ccg gcg cgc cct ggc ccg<br>Ala His Ala Pro Ala Pro Lys Ala Ala Lys Pro Ala Arg Pro Gly Pro<br>                20               25                   30 | | 156 |
| cgc tcc tgg atc ggg tat atc ctc cgc gag cag cgc ctc ctc ttc gtc<br>Arg Ser Trp Ile Gly Tyr Ile Leu Arg Glu Gln Arg Leu Leu Phe Val<br>                35               40                   45 | | 204 |
| ctc ctc ggc gcg ctc atc gcc acc acc ttc ttc ctc atc cgt ccc tac<br>Leu Leu Gly Ala Leu Ile Ala Thr Thr Phe Phe Leu Ile Arg Pro Tyr<br>        50                   55               60 | | 252 |
| ttc tcg ctc tcc ccg tcc tcc cac ctc ccc gac gtc cgc ccg ctc ttc<br>Phe Ser Leu Ser Pro Ser Ser His Leu Pro Asp Val Arg Pro Leu Phe<br> 65                   70               75 | | 300 |
| tcc ttc gcc gcc cgc tcc gct gtc ccg ccc ggc ttc cgc ccg ccc ccg<br>Ser Phe Ala Ala Arg Ser Ala Val Pro Pro Gly Phe Arg Pro Pro Pro<br> 80                  85               90               95 | | 348 |
| cgc cgc gtc gtc gtc aca ggc ggg gca ggg ttc gtc ggc agc cac ctc<br>Arg Arg Val Val Val Thr Gly Gly Ala Gly Phe Val Gly Ser His Leu<br>                   100              105              110 | | 396 |
| gtc gac cgg ctc cta gag cag ggg gac agc gtg atc gtg gtc gac aac<br>Val Asp Arg Leu Leu Glu Gln Gly Asp Ser Val Ile Val Val Asp Asn<br>             115                   120               125 | | 444 |
| ttc ttc acc ggc agg aag gag aac gtc gcg cac cac ctc cgg aac ccc<br>Phe Phe Thr Gly Arg Lys Glu Asn Val Ala His His Leu Arg Asn Pro<br>                 130               135               140 | | 492 |
| cgg ttc gag ctg ctc cgc cac gat gta gtc gaa cca atc ctc ctc gag<br>Arg Phe Glu Leu Leu Arg His Asp Val Val Glu Pro Ile Leu Leu Glu<br>145                  150                 155 | | 540 |
| gtc gac cgg atc tac cac ctc gca tgc ccc gcg tcg ccc gtt cat tac<br>Val Asp Arg Ile Tyr His Leu Ala Cys Pro Ala Ser Pro Val His Tyr<br>160                 165                 170               175 | | 588 |
| aag tat aac cca atc aag acg atc aag aca aat gtc atg gga act ttg<br>Lys Tyr Asn Pro Ile Lys Thr Ile Lys Thr Asn Val Met Gly Thr Leu<br>                  180               185              190 | | 636 |
| aat atg ttg ggt ctg gca aag cga gtt ggt gca agg ttt ttg ttg act<br>Asn Met Leu Gly Leu Ala Lys Arg Val Gly Ala Arg Phe Leu Leu Thr<br>             195                   200              205 | | 684 |
| agc aca agt gaa gtt tat ggt gat cca ctt gag cat cca cag aag gag<br>Ser Thr Ser Glu Val Tyr Gly Asp Pro Leu Glu His Pro Gln Lys Glu<br>                 210               215              220 | | 732 |
| tca tac tgg gga cac gtt aat cct att ggt gtt agg agc tgt tat gat<br>Ser Tyr Trp Gly His Val Asn Pro Ile Gly Val Arg Ser Cys Tyr Asp<br>225                  230                 235 | | 780 |
| gag ggg aag aga aca gct gag act tca act atg gac tat cat cgt ggt<br>Glu Gly Lys Arg Thr Ala Glu Thr Ser Thr Met Asp Tyr His Arg Gly<br>240                 245                 250               255 | | 828 |
| gct ggt gtt gag gtg cgt att gcc cgc att ttc aat aca tat ggt cct<br>Ala Gly Val Glu Val Arg Ile Ala Arg Ile Phe Asn Thr Tyr Gly Pro<br>                 260               265              270 | | 876 |
| cgt atg tgt ctc gat gat ggc cgt gtg gtc agc aat ttt gtt gca cag<br>Arg Met Cys Leu Asp Asp Gly Arg Val Val Ser Asn Phe Val Ala Gln<br>             275                   280              285 | | 924 |

-continued

```
gca cta cga aga caa cca atg acg gtt tat ggt gat gga aaa caa act      972
Ala Leu Arg Arg Gln Pro Met Thr Val Tyr Gly Asp Gly Lys Gln Thr
        290                 295                 300 cga agt ttc caa tat gtt tct gat ctg gtt gct gga ttg atg gct cta     1020
Arg Ser Phe Gln Tyr Val Ser Asp Leu Val Ala Gly Leu Met Ala Leu
305                 310                 315 atg gag agt gat cac att ggt cct ttc aac ttg gga aac cca gga gag     1068
Met Glu Ser Asp His Ile Gly Pro Phe Asn Leu Gly Asn Pro Gly Glu
320                 325                 330                 335 ttt acc atg ttg gag cta gca cag gtt gtg aag gaa aca att gac cca     1116
Phe Thr Met Leu Glu Leu Ala Gln Val Val Lys Glu Thr Ile Asp Pro
                340                 345                 350 atg gca acc att gaa ttc aaa ccc aac aca gct gat gat ccc cat atg     1164
Met Ala Thr Ile Glu Phe Lys Pro Asn Thr Ala Asp Asp Pro His Met
            355                 360                 365 aga aag ccg gat atc acc aag gct aag caa ctg cta cat tgg gag cca     1212
Arg Lys Pro Asp Ile Thr Lys Ala Lys Gln Leu Leu His Trp Glu Pro
        370                 375                 380 aac gtc tct ctc aga gaa ggc ctt ccg cta atg gtc aaa gac ttc cgt     1260
Asn Val Ser Leu Arg Glu Gly Leu Pro Leu Met Val Lys Asp Phe Arg
385                 390                 395 caa agg atc tcg gat gag taa tcgaggcaat cctacgatac tggtgaccgg       1311
Gln Arg Ile Ser Asp Glu  *
400                 405 tttgattctg aactatgctg caaatacagt cagaagctct ttatcgattg gagccatgca  1371
gtacagtgta ctgtgtacac agagactgta gaatcaccca ggcccattt ggaatgtggg   1431 gatccataca atttccactg atagtactg tttctgtgaa ataactgaaa agttcatggg   1491
aagttcgtgt taatctttt ttttatatc ttggtgggc agaacagaag cagtcaaata     1551 ttttttgtg catatgtgaa attccagagt tgtgggtggt gagagatagg atacaatgct   1611
gtatgtattt caggaacttc tgtaacacga gaacattcat catgtgaaaa aatgtaactg  1671
aatgtgttgg ccaaaaaaaa aaaaaaaaaa aaa                                1704
```

<210> SEQ ID NO 8
<211> LENGTH: 405
<212> TYPE: PRT
<213> ORGANISM: Zea mays

<400> SEQUENCE: 8

```
Met Lys Gln Leu His Lys Ser Ser Pro Thr Gln Ala Pro Ser Pro Ala
1               5                   10                  15

His Ala Pro Ala Pro Lys Ala Ala Lys Pro Ala Arg Pro Gly Pro Arg
            20                  25                  30

Ser Trp Ile Gly Tyr Ile Leu Arg Glu Gln Arg Leu Leu Phe Val Leu
        35                  40                  45

Leu Gly Ala Leu Ile Ala Thr Thr Phe Phe Leu Ile Arg Pro Tyr Phe
    50                  55                  60

Ser Leu Ser Pro Ser Ser His Leu Pro Asp Val Arg Pro Leu Phe Ser
65                  70                  75                  80

Phe Ala Ala Arg Ser Ala Val Pro Pro Gly Phe Arg Pro Pro Pro Arg
                85                  90                  95

Arg Val Val Val Thr Gly Gly Ala Gly Phe Val Gly Ser His Leu Val
            100                 105                 110

Asp Arg Leu Leu Glu Gln Gly Asp Ser Val Ile Val Val Asp Asn Phe
        115                 120                 125

Phe Thr Gly Arg Lys Glu Asn Val Ala His His Leu Arg Asn Pro Arg
```

-continued

```
            130                 135                 140
Phe Glu Leu Leu Arg His Asp Val Val Glu Pro Ile Leu Leu Glu Val
145                 150                 155                 160

Asp Arg Ile Tyr His Leu Ala Cys Pro Ala Ser Pro Val His Tyr Lys
                165                 170                 175

Tyr Asn Pro Ile Lys Thr Ile Lys Thr Asn Val Met Gly Thr Leu Asn
                180                 185                 190

Met Leu Gly Leu Ala Lys Arg Val Gly Ala Arg Phe Leu Leu Thr Ser
            195                 200                 205

Thr Ser Glu Val Tyr Gly Asp Pro Leu Glu His Pro Gln Lys Glu Ser
210                 215                 220

Tyr Trp Gly His Val Asn Pro Ile Gly Val Arg Ser Cys Tyr Asp Glu
225                 230                 235                 240

Gly Lys Arg Thr Ala Glu Thr Ser Thr Met Asp Tyr His Arg Gly Ala
                245                 250                 255

Gly Val Glu Val Arg Ile Ala Arg Ile Phe Asn Thr Tyr Gly Pro Arg
                260                 265                 270

Met Cys Leu Asp Asp Gly Arg Val Val Ser Asn Phe Val Ala Gln Ala
            275                 280                 285

Leu Arg Arg Gln Pro Met Thr Val Tyr Gly Asp Gly Lys Gln Thr Arg
        290                 295                 300

Ser Phe Gln Tyr Val Ser Asp Leu Val Ala Gly Leu Met Ala Leu Met
305                 310                 315                 320

Glu Ser Asp His Ile Gly Pro Phe Asn Leu Gly Asn Pro Gly Glu Phe
                325                 330                 335

Thr Met Leu Glu Leu Ala Gln Val Val Lys Glu Thr Ile Asp Pro Met
            340                 345                 350

Ala Thr Ile Glu Phe Lys Pro Asn Thr Ala Asp Asp Pro His Met Arg
                355                 360                 365

Lys Pro Asp Ile Thr Lys Ala Lys Gln Leu Leu His Trp Glu Pro Asn
        370                 375                 380

Val Ser Leu Arg Glu Gly Leu Pro Leu Met Val Lys Asp Phe Arg Gln
385                 390                 395                 400

Arg Ile Ser Asp Glu
                405

<210> SEQ ID NO 9
<211> LENGTH: 1631
<212> TYPE: DNA
<213> ORGANISM: Zea mays
<220> FEATURE:
<221> NAME/KEY: CDS
<222> LOCATION: (89)...(1405)
<223> OTHER INFORMATION: ZmUXS5

<400> SEQUENCE: 9
ccgcgagacc tgtccgaatc gcgtccaggt ccctcgctgg gagtttcgcc gagggccctc      60
ccgcctcccc cctagattca cgacggag atg gcg tcc gag ctc acc tac cgc       112
                                Met Ala Ser Glu Leu Thr Tyr Arg
                                  1               5 ggc ggc ggg gcg ttc acg gcc gcc agc gcc ggc gcc ggg ggc tac tcc      160
Gly Gly Gly Ala Phe Thr Ala Ala Ser Ala Gly Ala Gly Gly Tyr Ser
        10                  15                  20 ccg aag ccg tct aag ccg ctt gcg tgg ctg ccc cgc gcg gcc cgc tac      208
Pro Lys Pro Ser Lys Pro Leu Ala Trp Leu Pro Arg Ala Ala Arg Tyr
    25                  30                  35                  40
```

```
gcc gtc gcc gag aac cgc ccg ctc ttc gcg ctc gcc ggg atg ctc atc     256
Ala Val Ala Glu Asn Arg Pro Leu Phe Ala Leu Ala Gly Met Leu Ile
                45              50              55 gcc gcc gcc gtc atc tcc atc gcc tcc ccg tcc gcc tcc tcc tcc         304
Ala Ala Ala Val Ile Ser Ile Ala Ser Pro Ser Ala Ser Ser Ser
            60              65              70 tcc gcc gcc tcg tcc tac tcc aac aac aac ccg ctc gcc cgt ttc tcc     352
Ser Ala Ala Ser Ser Tyr Ser Asn Asn Asn Pro Leu Ala Arg Phe Ser
        75              80              85 gtc gag ccc gcc cac cac cgc gac gtg gcc acg cgg cac ttc gtc ggc     400
Val Glu Pro Ala His His Arg Asp Val Ala Thr Arg His Phe Val Gly
    90              95              100 ggc aag gtg ccg ctg ggc ctc aag agg aag gtg ctc cgc gtc ctc gtc     448
Gly Lys Val Pro Leu Gly Leu Lys Arg Lys Val Leu Arg Val Leu Val
105             110             115             120 acc ggc ggc gcc ggc ttc gtc ggc agc cac ctg gtg gac cgc ctc ctg     496
Thr Gly Gly Ala Gly Phe Val Gly Ser His Leu Val Asp Arg Leu Leu
                125             130             135 cag cgc gga gac agt gtc atc gtc gtc gac aac ttc ttc acc ggc cgc     544
Gln Arg Gly Asp Ser Val Ile Val Val Asp Asn Phe Phe Thr Gly Arg
            140             145             150 aag gac aac gtc ctg cac cac ctc ggc gac ccc aac ttc gag atg ata     592
Lys Asp Asn Val Leu His His Leu Gly Asp Pro Asn Phe Glu Met Ile
        155             160             165 cgc cac gac gtc gtc gag ccc atc ctg ctc gag gtc gac cag atc tac     640
Arg His Asp Val Val Glu Pro Ile Leu Leu Glu Val Asp Gln Ile Tyr
    170             175             180 cac ctc gcc tgc ccc gcg tcc ccc gtc cac tac aaa tac aac ccc atc     688
His Leu Ala Cys Pro Ala Ser Pro Val His Tyr Lys Tyr Asn Pro Ile
185             190             195             200 aaa aca atc aag acc aat gtg gtt ggg act ctg aac atg ctt gga ttg     736
Lys Thr Ile Lys Thr Asn Val Val Gly Thr Leu Asn Met Leu Gly Leu
                205             210             215 gca aag agg atc aat gct agg ttc ctc ctc acc agt acc agt gag gtc     784
Ala Lys Arg Ile Asn Ala Arg Phe Leu Leu Thr Ser Thr Ser Glu Val
            220             225             230 tat ggt gat ccc ctc cag cac ccg cag gtg gag act tac tgg ggc aat     832
Tyr Gly Asp Pro Leu Gln His Pro Gln Val Glu Thr Tyr Trp Gly Asn
        235             240             245 gtc aat ccc atc ggt gtc agg agc tgt tac gat gag ggc aag cgt aca     880
Val Asn Pro Ile Gly Val Arg Ser Cys Tyr Asp Glu Gly Lys Arg Thr
    250             255             260 gcc gaa acg ttg acc atg gat tac cac cgt ggt gcc aac ctt gag gtt     928
Ala Glu Thr Leu Thr Met Asp Tyr His Arg Gly Ala Asn Leu Glu Val
265             270             275             280 agg atc gca cgt atc ttc aac aca tat ggc cct cgc atg tgc att gac     976
Arg Ile Ala Arg Ile Phe Asn Thr Tyr Gly Pro Arg Met Cys Ile Asp
                285             290             295 gat ggc cgt gtt gtc agt aac ttc gtt gct cag gca ctg agg aag gag    1024
Asp Gly Arg Val Val Ser Asn Phe Val Ala Gln Ala Leu Arg Lys Glu
            300             305             310 ccc ttg acg gtt tat ggt gat gga aag caa acc agg agt ttc caa tat    1072
Pro Leu Thr Val Tyr Gly Asp Gly Lys Gln Thr Arg Ser Phe Gln Tyr
        315             320             325 gtt tct gat ctg gtc gag ggt ctg atg aag ctg atg gaa ggc gag cat    1120
Val Ser Asp Leu Val Glu Gly Leu Met Lys Leu Met Glu Gly Glu His
    330             335             340 gta gga cca ttt aac ctg ggc aac ccc ggc gag ttc acc atg ctg gag    1168
Val Gly Pro Phe Asn Leu Gly Asn Pro Gly Glu Phe Thr Met Leu Glu
345             350             355             360
```

-continued

| | |
|---|---|
| ctt gcc aag gtt gtc cag gac acc atc gac ccc aac gca cgg atc gag<br>Leu Ala Lys Val Val Gln Asp Thr Ile Asp Pro Asn Ala Arg Ile Glu<br>            365                    370                    375 | 1216 |
| ttc cgt cag aac acc cag gac gac cca cac aag cgc aag ccc gac atc<br>Phe Arg Gln Asn Thr Gln Asp Asp Pro His Lys Arg Lys Pro Asp Ile<br>        380                    385                    390 | 1264 |
| ggc cgt gcc aag gag ctc ctt ggg tgg gag ccg aag atc ccc ctc cgc<br>Gly Arg Ala Lys Glu Leu Leu Gly Trp Glu Pro Lys Ile Pro Leu Arg<br>395                    400                    405 | 1312 |
| gag ggc ctt ccc ctc atg gtc acc gac ttc cgc aag cgc atc ttc ggc<br>Glu Gly Leu Pro Leu Met Val Thr Asp Phe Arg Lys Arg Ile Phe Gly<br>410                      415                    420 | 1360 |
| gac caa gac acc gcg gct gcc acc acc gga aac cag caa ggc tag<br>Asp Gln Asp Thr Ala Ala Ala Thr Thr Gly Asn Gln Gln Gly *<br>425                    430                    435 | 1405 |
| gacggaagag gagcacggga cttggaaatt tttggtggcc tgcttctagc tgcttggtcg | 1465 |
| accctcctct ccttactgac aaaagctatg gccatgtagt tcgtcgggaa tgtgtcgctg | 1525 |
| aaataccttg gttgatgctg taatgctatt ctttctcctg tattttttct ctctcagttc | 1585 |
| gctcagccat tagctataca aaaaaaattc cagttgaaaa aaaaaa | 1631 |

<210> SEQ ID NO 10
<211> LENGTH: 438
<212> TYPE: PRT
<213> ORGANISM: Zea mays

<400> SEQUENCE: 10

Met Ala Ser Glu Leu Thr Tyr Arg Gly Gly Gly Ala Phe Thr Ala Ala
1               5                   10                  15

Ser Ala Gly Ala Gly Gly Tyr Ser Pro Lys Pro Ser Lys Pro Leu Ala
            20                  25                  30

Trp Leu Pro Arg Ala Ala Arg Tyr Ala Val Ala Glu Asn Arg Pro Leu
        35                  40                  45

Phe Ala Leu Ala Gly Met Leu Ile Ala Ala Val Ile Ser Ile Ala
    50                  55                  60

Ser Pro Ser Ala Ser Ser Ser Ser Ala Ala Ser Ser Tyr Ser Asn
65                  70                  75                  80

Asn Asn Pro Leu Ala Arg Phe Ser Val Glu Pro Ala His His Arg Asp
                85                  90                  95

Val Ala Thr Arg His Phe Val Gly Gly Lys Val Pro Leu Gly Leu Lys
            100                 105                 110

Arg Lys Val Leu Arg Val Leu Val Thr Gly Gly Ala Gly Phe Val Gly
        115                 120                 125

Ser His Leu Val Asp Arg Leu Leu Gln Arg Gly Asp Ser Val Ile Val
    130                 135                 140

Val Asp Asn Phe Phe Thr Gly Arg Lys Asp Asn Val Leu His His Leu
145                 150                 155                 160

Gly Asp Pro Asn Phe Glu Met Ile Arg His Asp Val Val Glu Pro Ile
                165                 170                 175

Leu Leu Glu Val Asp Gln Ile Tyr His Leu Ala Cys Pro Ala Ser Pro
            180                 185                 190

Val His Tyr Lys Tyr Asn Pro Ile Lys Thr Ile Lys Thr Asn Val Val
        195                 200                 205

Gly Thr Leu Asn Met Leu Gly Leu Ala Lys Arg Ile Asn Ala Arg Phe
    210                 215                 220

```
Leu Leu Thr Ser Thr Ser Glu Val Tyr Gly Asp Pro Leu Gln His Pro
225                 230                 235                 240

Gln Val Glu Thr Tyr Trp Gly Asn Val Asn Pro Ile Gly Val Arg Ser
                245                 250                 255

Cys Tyr Asp Glu Gly Lys Arg Thr Ala Glu Thr Leu Thr Met Asp Tyr
            260                 265                 270

His Arg Gly Ala Asn Leu Glu Val Arg Ile Ala Arg Ile Phe Asn Thr
        275                 280                 285

Tyr Gly Pro Arg Met Cys Ile Asp Asp Gly Arg Val Val Ser Asn Phe
    290                 295                 300

Val Ala Gln Ala Leu Arg Lys Glu Pro Leu Thr Val Tyr Gly Asp Gly
305                 310                 315                 320

Lys Gln Thr Arg Ser Phe Gln Tyr Val Ser Asp Leu Val Glu Gly Leu
                325                 330                 335

Met Lys Leu Met Glu Gly Glu His Val Gly Pro Phe Asn Leu Gly Asn
            340                 345                 350

Pro Gly Glu Phe Thr Met Leu Glu Leu Ala Lys Val Val Gln Asp Thr
        355                 360                 365

Ile Asp Pro Asn Ala Arg Ile Glu Phe Arg Gln Asn Thr Gln Asp Asp
    370                 375                 380

Pro His Lys Arg Lys Pro Asp Ile Gly Arg Ala Lys Glu Leu Leu Gly
385                 390                 395                 400

Trp Glu Pro Lys Ile Pro Leu Arg Glu Gly Leu Pro Leu Met Val Thr
                405                 410                 415

Asp Phe Arg Lys Arg Ile Phe Gly Asp Gln Asp Thr Ala Ala Ala Thr
            420                 425                 430

Thr Gly Asn Gln Gln Gly
        435

<210> SEQ ID NO 11
<211> LENGTH: 1773
<212> TYPE: DNA
<213> ORGANISM: Zea mays
<220> FEATURE:
<221> NAME/KEY: CDS
<222> LOCATION: (94)...(1434)
<223> OTHER INFORMATION: Zm UXS6

<400> SEQUENCE: 11
cccacgcgtc cgcccacgcg tccgatcgcg cccaggtccc tcgctgggag tttcgccgag        60
ggccctcccg cctcccctag attcacgacg gag atg gcg tcc gag ctc acc tac       114
                                    Met Ala Ser Glu Leu Thr Tyr
                                    1               5 cgc ggc ggc ggg acg tcc acg gcc gcc ggc gcc ggc gcc ggg gga tac        162
Arg Gly Gly Gly Thr Ser Thr Ala Ala Gly Ala Gly Ala Gly Gly Tyr
        10                  15                  20 tca ccg aag ccg tcc aag ccg ctc gcg tgg ctg ccc cgc gcg gcc cgc        210
Ser Pro Lys Pro Ser Lys Pro Leu Ala Trp Leu Pro Arg Ala Ala Arg
    25                  30                  35 tac gcc gtc gcc gag cat cgc ccg ctc ttc gcg ctc gcc ggg atg ctg        258
Tyr Ala Val Ala Glu His Arg Pro Leu Phe Ala Leu Ala Gly Met Leu
40                  45                  50                  55 atc gcc gcc gcc gtc atc tcc atc gcc tcc ccg tcc gcc tcc tcc tcc        306
Ile Ala Ala Ala Val Ile Ser Ile Ala Ser Pro Ser Ala Ser Ser Ser
                60                  65                  70 tcc tcc acc tcc acc tcc acc ggc ggc gcc gcc tcg tcc tac tcc aac        354
Ser Ser Thr Ser Thr Ser Thr Gly Gly Ala Ala Ser Ser Tyr Ser Asn
            75                  80                  85
```

```
                                                           -continued aac aac aat ccg ctc gcc cgc ttc ccc gtc gag ccc gcc cac cac cgc         402
Asn Asn Asn Pro Leu Ala Arg Phe Pro Val Glu Pro Ala His His Arg
         90                  95                 100 gac gtg gcc acg cgg cac ttc gtc ggc ggc aag gtg ccg ctg ggc ctc         450
Asp Val Ala Thr Arg His Phe Val Gly Gly Lys Val Pro Leu Gly Leu
    105                 110                 115 aag cgg aag gcg ctc cgc gtc ctc gtc acc ggc ggc gcc ggc ttc gtc         498
Lys Arg Lys Ala Leu Arg Val Leu Val Thr Gly Gly Ala Gly Phe Val
120                 125                 130                 135 ggc agc cac ctg gtg gac cgc ctc ctc gag cgc ggc gac agc gtt atc         546
Gly Ser His Leu Val Asp Arg Leu Leu Glu Arg Gly Asp Ser Val Ile
                140                 145                 150 gtc gtc gat aac ttc ttc acc ggc cgc aag gac aac gtt ctt cac cac         594
Val Val Asp Asn Phe Phe Thr Gly Arg Lys Asp Asn Val Leu His His
            155                 160                 165 ctc aac gac cca aac ttc gag atg atc cgc cac gat gtc gtc gag ccc         642
Leu Asn Asp Pro Asn Phe Glu Met Ile Arg His Asp Val Val Glu Pro
        170                 175                 180 atc ctc ctc gag gtc gac cag atc tac cac ctc gcc tgc ccg gcg tcc         690
Ile Leu Leu Glu Val Asp Gln Ile Tyr His Leu Ala Cys Pro Ala Ser
    185                 190                 195 ccc gtc cac tac aaa tac aac ccc atc aag aca atc aag acc aat gtg         738
Pro Val His Tyr Lys Tyr Asn Pro Ile Lys Thr Ile Lys Thr Asn Val
200                 205                 210                 215 gtt ggg act ctg aac atg ctc gga tta gca aag agg atc aac gcc agg         786
Val Gly Thr Leu Asn Met Leu Gly Leu Ala Lys Arg Ile Asn Ala Arg
                220                 225                 230 ttc ctc ctc acc agt acc agt gag gtc tat ggt gat cct ctc cag cac         834
Phe Leu Leu Thr Ser Thr Ser Glu Val Tyr Gly Asp Pro Leu Gln His
            235                 240                 245 ccg cag gtg gag act tac tgg ggc aat gtc aat ccc atc ggt gtc agg         882
Pro Gln Val Glu Thr Tyr Trp Gly Asn Val Asn Pro Ile Gly Val Arg
        250                 255                 260 agc tgt tac gat gag ggc aag cgt aca gct gaa acg ttg acc atg gat         930
Ser Cys Tyr Asp Glu Gly Lys Arg Thr Ala Glu Thr Leu Thr Met Asp
    265                 270                 275 tac cac cgt ggt gcc aac ctt gag gtt agg atc gca cgt atc ttc aat         978
Tyr His Arg Gly Ala Asn Leu Glu Val Arg Ile Ala Arg Ile Phe Asn
280                 285                 290                 295 aca tat ggc cct cgc atg tgc att gac gat ggc cgt gtt gtc agt aac        1026
Thr Tyr Gly Pro Arg Met Cys Ile Asp Asp Gly Arg Val Val Ser Asn
                300                 305                 310 ttt gtt gct cag gca ctg agg aag gag ccc ttg acg gtt tat ggt gat        1074
Phe Val Ala Gln Ala Leu Arg Lys Glu Pro Leu Thr Val Tyr Gly Asp
            315                 320                 325 gga aag caa acc agg agt ttc caa tat gtt tct gat ctg gtt gag ggt        1122
Gly Lys Gln Thr Arg Ser Phe Gln Tyr Val Ser Asp Leu Val Glu Gly
        330                 335                 340 ctg atg aag ctg atg gaa ggc gag cat gtg ggg cca ttc aac ctg ggt        1170
Leu Met Lys Leu Met Glu Gly Glu His Val Gly Pro Phe Asn Leu Gly
    345                 350                 355 aac cct ggc gag ttc acc atg ctt gag ctt gcc aag gtt gtc cag gac        1218
Asn Pro Gly Glu Phe Thr Met Leu Glu Leu Ala Lys Val Val Gln Asp
360                 365                 370                 375 acc atc gac ccc aac gca cgg atc gag ttc cgc aag aac acc cag gac        1266
Thr Ile Asp Pro Asn Ala Arg Ile Glu Phe Arg Lys Asn Thr Gln Asp
                380                 385                 390 gac ccg cac aag cgc aag ccc gac atc agc cgc gcc aag gag ttc ctc        1314
Asp Pro His Lys Arg Lys Pro Asp Ile Ser Arg Ala Lys Glu Phe Leu
```

-continued

```
                395                 400                 405
ggg tgg gag ccg aag atc ccc ctg cgt gag ggc ctt ccc ctc atg gtc    1362
Gly Trp Glu Pro Lys Ile Pro Leu Arg Glu Gly Leu Pro Leu Met Val
        410                 415                 420 tcc gac ttc cgc aag cgc atc ttc ggc gac caa gac gct gct gcc acc    1410
Ser Asp Phe Arg Lys Arg Ile Phe Gly Asp Gln Asp Ala Ala Ala Thr
425                 430                 435 acc acc gga aac cag caa ggt tag gatgaaggag cgcacatgac atggaaattt   1464
Thr Thr Gly Asn Gln Gln Gly *
440                 445 ttggtggccc tgcttctagc tgcttggttg ctctctcctt actgacaaaa gctatgggcc   1524
acgtagttcg ttgggaatgt gttactggaa tacctcggca cggctgatgc tgtaatgcca   1584
ttcttttttt cccctgtatt ttttcttcct cagttctctc agtccttagc tatacaaaaa   1644
aagttcagtt gaacagttgg agatgaaccc ggatgatcta attctttgtt gagagcatag   1704
catcatatat atggtataaa tcctgtcatt ttgcaaatgt aaaaaaaaaa aaaaaaaaa    1764 aaaaaaaaa                                                          1773

<210> SEQ ID NO 12
<211> LENGTH: 446
<212> TYPE: PRT
<213> ORGANISM: Zea mays

<400> SEQUENCE: 12

Met Ala Ser Glu Leu Thr Tyr Arg Gly Gly Gly Thr Ser Thr Ala Ala
1               5                   10                  15

Gly Ala Gly Ala Gly Gly Tyr Ser Pro Lys Pro Ser Lys Pro Leu Ala
            20                  25                  30

Trp Leu Pro Arg Ala Ala Arg Tyr Ala Val Ala Glu His Arg Pro Leu
        35                  40                  45

Phe Ala Leu Ala Gly Met Leu Ile Ala Ala Val Ile Ser Ile Ala
    50                  55                  60

Ser Pro Ser Ala Ser Ser Ser Ser Thr Ser Thr Ser Thr Gly Gly
65              70                  75                  80

Ala Ala Ser Ser Tyr Ser Asn Asn Asn Pro Leu Ala Arg Phe Pro
            85                  90                  95

Val Glu Pro Ala His His Arg Asp Val Ala Thr Arg His Phe Val Gly
            100                 105                 110

Gly Lys Val Pro Leu Gly Leu Lys Arg Lys Ala Leu Arg Val Leu Val
            115                 120                 125

Thr Gly Gly Ala Gly Phe Val Gly Ser His Leu Val Asp Arg Leu Leu
    130                 135                 140

Glu Arg Gly Asp Ser Val Ile Val Val Asp Asn Phe Phe Thr Gly Arg
145                 150                 155                 160

Lys Asp Asn Val Leu His His Leu Asn Asp Pro Asn Phe Glu Met Ile
                165                 170                 175

Arg His Asp Val Val Glu Pro Ile Leu Leu Glu Val Asp Gln Ile Tyr
            180                 185                 190

His Leu Ala Cys Pro Ala Ser Pro Val His Tyr Lys Tyr Asn Pro Ile
        195                 200                 205

Lys Thr Ile Lys Thr Asn Val Val Gly Thr Leu Asn Met Leu Gly Leu
    210                 215                 220

Ala Lys Arg Ile Asn Ala Arg Phe Leu Leu Thr Ser Thr Ser Glu Val
225                 230                 235                 240
```

```
Tyr Gly Asp Pro Leu Gln His Pro Gln Val Glu Thr Tyr Trp Gly Asn
                245                 250                 255

Val Asn Pro Ile Gly Val Arg Ser Cys Tyr Asp Glu Gly Lys Arg Thr
            260                 265                 270

Ala Glu Thr Leu Thr Met Asp Tyr His Arg Gly Ala Asn Leu Glu Val
        275                 280                 285

Arg Ile Ala Arg Ile Phe Asn Thr Tyr Gly Pro Arg Met Cys Ile Asp
    290                 295                 300

Asp Gly Arg Val Val Ser Asn Phe Val Ala Gln Ala Leu Arg Lys Glu
305                 310                 315                 320

Pro Leu Thr Val Tyr Gly Asp Gly Lys Gln Thr Arg Ser Phe Gln Tyr
                325                 330                 335

Val Ser Asp Leu Val Glu Gly Leu Met Lys Leu Met Glu Gly Glu His
            340                 345                 350

Val Gly Pro Phe Asn Leu Gly Asn Pro Gly Glu Phe Thr Met Leu Glu
        355                 360                 365

Leu Ala Lys Val Val Gln Asp Thr Ile Asp Pro Asn Ala Arg Ile Glu
    370                 375                 380

Phe Arg Lys Asn Thr Gln Asp Asp Pro His Lys Arg Lys Pro Asp Ile
385                 390                 395                 400

Ser Arg Ala Lys Glu Phe Leu Gly Trp Glu Pro Lys Ile Pro Leu Arg
                405                 410                 415

Glu Gly Leu Pro Leu Met Val Ser Asp Phe Arg Lys Arg Ile Phe Gly
            420                 425                 430

Asp Gln Asp Ala Ala Ala Thr Thr Thr Gly Asn Gln Gln Gly
        435                 440                 445

<210> SEQ ID NO 13
<211> LENGTH: 1677
<212> TYPE: DNA
<213> ORGANISM: Zea mays
<220> FEATURE:
<221> NAME/KEY: CDS
<222> LOCATION: (74)...(1405)
<223> OTHER INFORMATION: Zm UXS7

<400> SEQUENCE: 13
ccgaatcgcg cccaggtccc tcgctgggag tttcgccgag ggccctcccg cctcccctag      60
attcacgacg gag atg gcg tcc gag ctc acc tac cgc ggc ggc ggg gcg       109
            Met Ala Ser Glu Leu Thr Tyr Arg Gly Gly Gly Ala
              1               5                  10 tcc acg gcc gcc ggc gcc ggc gcc ggg gga tac tca ccg aag ccg tcc      157
Ser Thr Ala Ala Gly Ala Gly Ala Gly Gly Tyr Ser Pro Lys Pro Ser
         15                  20                  25 aag ccg ctc gcg tgg ctg ccc cgc gcg gcc cgc tac gcc gtc gcc gag      205
Lys Pro Leu Ala Trp Leu Pro Arg Ala Ala Arg Tyr Ala Val Ala Glu
     30                  35                  40 cat cgc ccg ctc ttc gcg ctc gcc ggg atg ctg atc gcc gcc gcc gtc      253
His Arg Pro Leu Phe Ala Leu Ala Gly Met Leu Ile Ala Ala Ala Val
 45                  50                  55                  60 atc tcc atc gcc tcc ccg tcc gcc tcc tcc atc tcc acc tcc acc          301
Ile Ser Ile Ala Ser Pro Ser Ala Ser Ser Ile Ser Thr Ser Thr
                 65                  70                  75 ggc ggc gct gcc tcg tcc tac tcc aac aac aac aat ccg ctc gcc cgc      349
Gly Gly Ala Ala Ser Ser Tyr Ser Asn Asn Asn Asn Pro Leu Ala Arg
             80                  85                  90 ttc ccc gtc gag ccc gcc cac cac cgc gac gtg gcc acg cgg cac ttc      397
Phe Pro Val Glu Pro Ala His His Arg Asp Val Ala Thr Arg His Phe
```

-continued

```
                    95                      100                      105
gtc ggc ggc aag gtg ccg ctg ggc ctc aag cgg aag gcg ctc cgc gtc        445
Val Gly Gly Lys Val Pro Leu Gly Leu Lys Arg Lys Ala Leu Arg Val
            110                 115                 120 ctc gtc acc ggc gcc ggc ttc gtc ggc agc cac ctg gtg gac cgc            493
Leu Val Thr Gly Ala Gly Phe Val Gly Ser His Leu Val Asp Arg
125                 130                 135                 140 ctc ctc gag cgc ggc gac agc gtt att gtc gtc gat aac ttc ttc acc        541
Leu Leu Glu Arg Gly Asp Ser Val Ile Val Val Asp Asn Phe Phe Thr
                        145                 150                 155 ggc cgc aag gac aac gtt ctg cac cac ctc aac gac cca aac ttc gag        589
Gly Arg Lys Asp Asn Val Leu His His Leu Asn Asp Pro Asn Phe Glu
                160                 165                 170 atg atc cgc cac gat gtc gtc gag ccc atc ctc ctc gag gtc gac cag        637
Met Ile Arg His Asp Val Val Glu Pro Ile Leu Leu Glu Val Asp Gln
            175                 180                 185 atc tac cac ctc gcc tgc ccg gcg tcc ccc gtc cac tac aaa tac aac        685
Ile Tyr His Leu Ala Cys Pro Ala Ser Pro Val His Tyr Lys Tyr Asn
        190                 195                 200 ccc atc aag aca atc aag acc aat gtg gtt ggg act ctg aac atg ctc        733
Pro Ile Lys Thr Ile Lys Thr Asn Val Val Gly Thr Leu Asn Met Leu
205                 210                 215                 220 gga tta gca aag agg atc aac gcc agg ttc ctc ctc acc agt acc agt        781
Gly Leu Ala Lys Arg Ile Asn Ala Arg Phe Leu Leu Thr Ser Thr Ser
                        225                 230                 235 gag gtc tat ggt gat cct ctc cag cac ccg cag gtg gag act tac tgg        829
Glu Val Tyr Gly Asp Pro Leu Gln His Pro Gln Val Glu Thr Tyr Trp
                240                 245                 250 ggc aat gtc aat ccc atc ggt gtc agg agc tgt tac gat gag ggc aag        877
Gly Asn Val Asn Pro Ile Gly Val Arg Ser Cys Tyr Asp Glu Gly Lys
            255                 260                 265 cgt aca gct gaa acg ttg acc atg gat tac cac cgt ggt gcc aac ctt        925
Arg Thr Ala Glu Thr Leu Thr Met Asp Tyr His Arg Gly Ala Asn Leu
        270                 275                 280 gag gtt agg atc gca cgt atc ttc aac aca tat ggc cct cgc atg tgc        973
Glu Val Arg Ile Ala Arg Ile Phe Asn Thr Tyr Gly Pro Arg Met Cys
285                 290                 295                 300 att gac gat ggc cgt gtt gtc agt aac ttt gtt gct cag gca ctg agg       1021
Ile Asp Asp Gly Arg Val Val Ser Asn Phe Val Ala Gln Ala Leu Arg
                        305                 310                 315 aag gag ccc ttg acg gtt tat ggt gat gga aag caa acc agg agt ttc       1069
Lys Glu Pro Leu Thr Val Tyr Gly Asp Gly Lys Gln Thr Arg Ser Phe
                320                 325                 330 caa tat gtt tct gat ctg gtt gag ggt ctg atg aag ctg atg gaa ggc       1117
Gln Tyr Val Ser Asp Leu Val Glu Gly Leu Met Lys Leu Met Glu Gly
            335                 340                 345 gag cat gtg ggg cca ttc aac ctg ggt aac cct ggc gag ttc acc atg       1165
Glu His Val Gly Pro Phe Asn Leu Gly Asn Pro Gly Glu Phe Thr Met
350                 355                 360 ctt gag ctt gcg aag gtt gtc cag gac acc atc gac ccc aac gca cgg       1213
Leu Glu Leu Ala Lys Val Val Gln Asp Thr Ile Asp Pro Asn Ala Arg
365                 370                 375                 380 atc gag ttc cgc aag aac acc cag gac gac ccg cac aag cgc aag ccc       1261
Ile Glu Phe Arg Lys Asn Thr Gln Asp Asp Pro His Lys Arg Lys Pro
                        385                 390                 395 gac atc agc cgc gcc aag gag ttc ctc ggg tgg gag ccg aag atc ccc       1309
Asp Ile Ser Arg Ala Lys Glu Phe Leu Gly Trp Glu Pro Lys Ile Pro
                400                 405                 410 ctg cgt gag ggc ctt ccc ctc atg gtc tcc gac ttc cgc aag cgc atc       1357
```

-continued

```
            Leu Arg Glu Gly Leu Pro Leu Met Val Ser Asp Phe Arg Lys Arg Ile
                    415                 420                 425 ttc ggc gac caa gac gct act gcc acc acc gga aac cag caa ggt tag        1405
Phe Gly Asp Gln Asp Ala Thr Ala Thr Thr Gly Asn Gln Gln Gly *
        430                 435                 440 gatgaaggag cgcacatgac atggaaattt ttggtggccc tgcttctagc tgcttggttg      1465
ctctctcctt actgacaaaa gctatgggcc acgtagttcg ttgggaatgt gttactggaa      1525
tacctcggct gatgctgtaa tgccattctt tttttcccct gtattttttc tttctcagtt      1585
ctctcagtcc ttagctatac aaaaaaaaaa gttcagttga acagttggag ataaaccagg      1645
atgatctaat tcaaaaaaaa aaaaaaaaaa aa                                    1677

<210> SEQ ID NO 14
<211> LENGTH: 443
<212> TYPE: PRT
<213> ORGANISM: Zea mays

<400> SEQUENCE: 14

Met Ala Ser Glu Leu Thr Tyr Arg Gly Gly Gly Ala Ser Thr Ala Ala
 1               5                  10                  15

Gly Ala Gly Ala Gly Gly Tyr Ser Pro Lys Pro Ser Lys Pro Leu Ala
            20                  25                  30

Trp Leu Pro Arg Ala Ala Arg Tyr Ala Val Ala Glu His Arg Pro Leu
        35                  40                  45

Phe Ala Leu Ala Gly Met Leu Ile Ala Ala Val Ile Ser Ile Ala
    50                  55                  60

Ser Pro Ser Ala Ser Ser Ile Ser Thr Ser Thr Gly Gly Ala Ala
65                  70                  75                  80

Ser Ser Tyr Ser Asn Asn Asn Asn Pro Leu Ala Arg Phe Pro Val Glu
                85                  90                  95

Pro Ala His His Arg Asp Val Ala Thr Arg His Phe Val Gly Gly Lys
            100                 105                 110

Val Pro Leu Gly Leu Lys Arg Lys Ala Leu Arg Val Leu Val Thr Gly
        115                 120                 125

Gly Ala Gly Phe Val Gly Ser His Leu Val Asp Arg Leu Leu Glu Arg
    130                 135                 140

Gly Asp Ser Val Ile Val Val Asp Asn Phe Phe Thr Gly Arg Lys Asp
145                 150                 155                 160

Asn Val Leu His His Leu Asn Asp Pro Asn Phe Glu Met Ile Arg His
                165                 170                 175

Asp Val Val Glu Pro Ile Leu Leu Glu Val Asp Gln Ile Tyr His Leu
            180                 185                 190

Ala Cys Pro Ala Ser Pro Val His Tyr Lys Tyr Asn Pro Ile Lys Thr
        195                 200                 205

Ile Lys Thr Asn Val Val Gly Thr Leu Asn Met Leu Gly Leu Ala Lys
    210                 215                 220

Arg Ile Asn Ala Arg Phe Leu Leu Thr Ser Thr Ser Glu Val Tyr Gly
225                 230                 235                 240

Asp Pro Leu Gln His Pro Gln Val Glu Thr Tyr Trp Gly Asn Val Asn
                245                 250                 255

Pro Ile Gly Val Arg Ser Cys Tyr Asp Glu Gly Lys Arg Thr Ala Glu
            260                 265                 270

Thr Leu Thr Met Asp Tyr His Arg Gly Ala Asn Leu Glu Val Arg Ile
        275                 280                 285
```

-continued

```
Ala Arg Ile Phe Asn Thr Tyr Gly Pro Arg Met Cys Ile Asp Asp Gly
        290                 295                 300

Arg Val Val Ser Asn Phe Val Ala Gln Ala Leu Arg Lys Glu Pro Leu
305                 310                 315                 320

Thr Val Tyr Gly Asp Gly Lys Gln Thr Arg Ser Phe Gln Tyr Val Ser
                325                 330                 335

Asp Leu Val Glu Gly Leu Met Lys Leu Met Glu Gly Glu His Val Gly
            340                 345                 350

Pro Phe Asn Leu Gly Asn Pro Gly Glu Phe Thr Met Leu Glu Leu Ala
        355                 360                 365

Lys Val Val Gln Asp Thr Ile Asp Pro Asn Ala Arg Ile Glu Phe Arg
370                 375                 380

Lys Asn Thr Gln Asp Asp Pro His Lys Arg Lys Pro Asp Ile Ser Arg
385                 390                 395                 400

Ala Lys Glu Phe Leu Gly Trp Glu Pro Lys Ile Pro Leu Arg Glu Gly
                405                 410                 415

Leu Pro Leu Met Val Ser Asp Phe Arg Lys Arg Ile Phe Gly Asp Gln
            420                 425                 430

Asp Ala Thr Ala Thr Thr Gly Asn Gln Gln Gly
        435                 440

<210> SEQ ID NO 15
<211> LENGTH: 1583
<212> TYPE: DNA
<213> ORGANISM: Zea mays
<220> FEATURE:
<221> NAME/KEY: CDS
<222> LOCATION: (58)...(1347)
<223> OTHER INFORMATION: Zm UXS8

<400> SEQUENCE: 15
cttcacgatc tggtccaaag ccccaactca aatttacatc caggccattc gccggag atg      60
                                                               Met
                                                                1 gcg tcg gag ctg acg tac cgc ggc ggc agc gtg gcg cca ggc tcc gcc        108
Ala Ser Glu Leu Thr Tyr Arg Gly Gly Ser Val Ala Pro Gly Ser Ala
        5                   10                  15 tcc aac ggt ggg gaa tac tcc ccg aag tcc tcc aag ccg ctc tcc tgg        156
Ser Asn Gly Gly Glu Tyr Ser Pro Lys Ser Ser Lys Pro Leu Ser Trp
    20                  25                  30 ctc gcc cgc gcc gcg cgc tac gcc gcc gcc gag cac cgc ccc gtc ttc        204
Leu Ala Arg Ala Ala Arg Tyr Ala Ala Ala Glu His Arg Pro Val Phe
 35                 40                  45 gcc ctc gcc ggc atg ctc ttc gct gcc gct atc ttc acc ttc tct tcc        252
Ala Leu Ala Gly Met Leu Phe Ala Ala Ala Ile Phe Thr Phe Ser Ser
 50                 55                  60                  65 ccc tcc act tta tct ccg tcc gaa ccc gcc gcg tcg gtc ggc ttc aac        300
Pro Ser Thr Leu Ser Pro Ser Glu Pro Ala Ala Ser Val Gly Phe Asn
                70                  75                  80 cac ctt gcc gtc agc ggg cac ccg tcc ttc cgc gag tcc gtc ggc ggg        348
His Leu Ala Val Ser Gly His Pro Ser Phe Arg Glu Ser Val Gly Gly
            85                  90                  95 aag gtt ccc ctg ggg ctg cgt cgg cgc gcg ctg cgg gtg ctc gtg acg        396
Lys Val Pro Leu Gly Leu Arg Arg Arg Ala Leu Arg Val Leu Val Thr
        100                 105                 110 ggc ggc gcc ggg ttc gtg ggg agc cac ctg gtg gac cgg ctg ttg gag        444
Gly Gly Ala Gly Phe Val Gly Ser His Leu Val Asp Arg Leu Leu Glu
    115                 120                 125 cgc ggc gac agc gtg att gtg gtg gat aac ttc ttc acg ggg cgc aag        492
```

```
                Arg Gly Asp Ser Val Ile Val Asp Asn Phe Phe Thr Gly Arg Lys
                130                 135                 140                 145 gcc aac gtg gcg cac cat ctc cag aac ccc agg ttc gag gtg atc cgc              540
Gly Asn Val Ala His His Leu Gln Asn Pro Arg Phe Glu Val Ile Arg
                150                 155                 160 cac gac gtc gtc gag ccc ata ctg ctc gag gtc gac cag atc tac cac              588
His Asp Val Val Glu Pro Ile Leu Leu Glu Val Asp Gln Ile Tyr His
            165                 170                 175 ctt gcc tgt cca gcc agc ccc gtg cac tac aag tac aac ccc atc aag              636
Leu Ala Cys Pro Ala Ser Pro Val His Tyr Lys Tyr Asn Pro Ile Lys
            180                 185                 190 acc atc aag aca aat gtt gtt gga aca ctg aac atg ctt gga ttg gcc              684
Thr Ile Lys Thr Asn Val Val Gly Thr Leu Asn Met Leu Gly Leu Ala
            195                 200                 205 aag agg att ggg gca agg ttc cta ctt aca agc acc agt gag gtt tat              732
Lys Arg Ile Gly Ala Arg Phe Leu Leu Thr Ser Thr Ser Glu Val Tyr
210                 215                 220                 225 ggt gat ccc ctc cag cac cct cag gtg gaa acc tat tgg ggc aat gtc              780
Gly Asp Pro Leu Gln His Pro Gln Val Glu Thr Tyr Trp Gly Asn Val
                230                 235                 240 aac cct ata ggt gtc agg agc tgc tat gat gag gga aag cgt aca gct              828
Asn Pro Ile Gly Val Arg Ser Cys Tyr Asp Glu Gly Lys Arg Thr Ala
            245                 250                 255 gaa aca tta acc atg gac tac cat cgt ggt gcc aac ctt gag gta agg              876
Glu Thr Leu Thr Met Asp Tyr His Arg Gly Ala Asn Leu Glu Val Arg
            260                 265                 270 att gcc cgg atc ttt aac aca tat ggt cct cgc atg tgc att gat gac              924
Ile Ala Arg Ile Phe Asn Thr Tyr Gly Pro Arg Met Cys Ile Asp Asp
275                 280                 285 ggc cgt gtt gtc agt aat ttc gtt gct cag gcg ctg agg aag gag cct              972
Gly Arg Val Val Ser Asn Phe Val Ala Gln Ala Leu Arg Lys Glu Pro
290                 295                 300                 305 ttg aca gtc tat ggt gat ggc aag cag act agg agc ttt caa tat gtc             1020
Leu Thr Val Tyr Gly Asp Gly Lys Gln Thr Arg Ser Phe Gln Tyr Val
                310                 315                 320 tca gat ttg gtg gaa ggg ctg atg aag ctc atg gaa ggg gag cac att             1068
Ser Asp Leu Val Glu Gly Leu Met Lys Leu Met Glu Gly Glu His Ile
            325                 330                 335 ggg ccg ttc aac ctc ggc aac cct gga gaa ttc agc atg ctg gag ctg             1116
Gly Pro Phe Asn Leu Gly Asn Pro Gly Glu Phe Ser Met Leu Glu Leu
            340                 345                 350 gct aag gtg gtc cag gac acc atc gac cca gag gcg cac atc gag ttc             1164
Ala Lys Val Val Gln Asp Thr Ile Asp Pro Glu Ala His Ile Glu Phe
            355                 360                 365 cgt ccg aac acc gca gat gat ccg cac aag cgc aag cct gac atc agc             1212
Arg Pro Asn Thr Ala Asp Asp Pro His Lys Arg Lys Pro Asp Ile Ser
370                 375                 380                 385 cgc gcg aaa gag ctc ctc ggc tgg gag ccc aag gtt ccc ctc cgt gag             1260
Arg Ala Lys Glu Leu Leu Gly Trp Glu Pro Lys Val Pro Leu Arg Glu
                390                 395                 400 ggc ctt ccc cgc atg gtc act gac ttc cgc aaa cgt atc ttc ggg gac             1308
Gly Leu Pro Arg Met Val Thr Asp Phe Arg Lys Arg Ile Phe Gly Asp
            405                 410                 415 cag gaa ggg tcc acc gag tca gct ggt ggc ctt tct taa gtgctcaaaa             1357
Gln Glu Gly Ser Thr Glu Ser Ala Gly Gly Leu Ser *
            420                 425 cttgttgaag tgacacgttt gtatggtata tgacttgata cagttttggc gctgtgctct           1417
atacgtagtt gttatatagg gatataaatg tttgttaaag tacggaaaat agcctggcac           1477
```

```
gctatactat gtaacgacgt accattttgt aatgtcattg ttaacgggtt atccagaatg    1537
ctaatagcgt tataatctta cattacatat aaaaaaaaaa aaaaaa                   1583
```

<210> SEQ ID NO 16
<211> LENGTH: 429
<212> TYPE: PRT
<213> ORGANISM: Zea mays

<400> SEQUENCE: 16

```
Met Ala Ser Glu Leu Thr Tyr Arg Gly Gly Ser Val Ala Pro Gly Ser
 1               5                  10                  15

Ala Ser Asn Gly Gly Glu Tyr Ser Pro Lys Ser Ser Lys Pro Leu Ser
            20                  25                  30

Trp Leu Ala Arg Ala Ala Arg Tyr Ala Ala Ala Glu His Arg Pro Val
        35                  40                  45

Phe Ala Leu Ala Gly Met Leu Phe Ala Ala Ile Phe Thr Phe Ser
    50                  55                  60

Ser Pro Ser Thr Leu Ser Pro Ser Glu Pro Ala Ala Ser Val Gly Phe
65                  70                  75                  80

Asn His Leu Ala Val Ser Gly His Pro Ser Phe Arg Glu Ser Val Gly
                85                  90                  95

Gly Lys Val Pro Leu Gly Leu Arg Arg Arg Ala Leu Arg Val Leu Val
            100                 105                 110

Thr Gly Gly Ala Gly Phe Val Gly Ser His Leu Val Asp Arg Leu Leu
        115                 120                 125

Glu Arg Gly Asp Ser Val Ile Val Val Asp Asn Phe Phe Thr Gly Arg
    130                 135                 140

Lys Gly Asn Val Ala His His Leu Gln Asn Pro Arg Phe Glu Val Ile
145                 150                 155                 160

Arg His Asp Val Val Glu Pro Ile Leu Leu Glu Val Asp Gln Ile Tyr
                165                 170                 175

His Leu Ala Cys Pro Ala Ser Pro Val His Tyr Lys Tyr Asn Pro Ile
            180                 185                 190

Lys Thr Ile Lys Thr Asn Val Val Gly Thr Leu Asn Met Leu Gly Leu
        195                 200                 205

Ala Lys Arg Ile Gly Ala Arg Phe Leu Leu Thr Ser Thr Ser Glu Val
    210                 215                 220

Tyr Gly Asp Pro Leu Gln His Pro Gln Val Glu Thr Tyr Trp Gly Asn
225                 230                 235                 240

Val Asn Pro Ile Gly Val Arg Ser Cys Tyr Asp Glu Gly Lys Arg Thr
                245                 250                 255

Ala Glu Thr Leu Thr Met Asp Tyr His Arg Gly Ala Asn Leu Glu Val
            260                 265                 270

Arg Ile Ala Arg Ile Phe Asn Thr Tyr Gly Pro Arg Met Cys Ile Asp
        275                 280                 285

Asp Gly Arg Val Val Ser Asn Phe Val Ala Gln Ala Leu Arg Lys Glu
    290                 295                 300

Pro Leu Thr Val Tyr Gly Asp Gly Lys Gln Thr Arg Ser Phe Gln Tyr
305                 310                 315                 320

Val Ser Asp Leu Val Glu Gly Leu Met Lys Leu Met Glu Gly Glu His
                325                 330                 335

Ile Gly Pro Phe Asn Leu Gly Asn Pro Gly Glu Phe Ser Met Leu Glu
            340                 345                 350

Leu Ala Lys Val Val Gln Asp Thr Ile Asp Pro Glu Ala His Ile Glu
```

```
                  355                 360                 365
Phe Arg Pro Asn Thr Ala Asp Asp Pro His Lys Arg Lys Pro Asp Ile
            370                 375                 380

Ser Arg Ala Lys Glu Leu Leu Gly Trp Glu Pro Lys Val Pro Leu Arg
385                 390                 395                 400

Glu Gly Leu Pro Arg Met Val Thr Asp Phe Arg Lys Arg Ile Phe Gly
                405                 410                 415

Asp Gln Glu Gly Ser Thr Glu Ser Ala Gly Gly Leu Ser
            420                 425

<210> SEQ ID NO 17
<211> LENGTH: 422
<212> TYPE: DNA
<213> ORGANISM: Artificial Sequence
<220> FEATURE:
<223> OTHER INFORMATION: Inverted repeat region of Zm UXS6

<400> SEQUENCE: 17
tcgaggaggc ggtccaccag gtggctgccg acgaagccgg cgccgccggt gacgaggacg      60
cggagcgcct tccgcttgag gcccagcggc accttgccgc cgacgaagtg ccgcgtggcc     120
acgtcgcggt ggtgggcggg ctcgacgggg aagcgggcga gcggattgtt gttgttggag     180
taggacgagg cggcgccgcc ggtggaggtg gaggtgaggg aggaggagga ggcggacggg     240
gaggcgatgg agatgacggc ggcggcgatc agcatcccgg cgagcgcgaa gagcgggcga     300
tgctcggcga cggcgtagcg ggccgcgcgg ggcagccacg cgagcggctt ggacggcttc     360
ggtgagtatc ccccggcgcc ggcgccggcg ccgtggacg tcccgccgcc gcggtaggtg      420
ag                                                                   422

<210> SEQ ID NO 18
<211> LENGTH: 865
<212> TYPE: DNA
<213> ORGANISM: Artificial Sequence
<220> FEATURE:
<223> OTHER INFORMATION: Inverted repeat region of Zm UXS2

<400> SEQUENCE: 18
catccgtcat gatgtcaccg agccgcttct tgtggaagtt gaccaaatct atcaccttgc      60
ttgccctgct tcaccaatct tctacaagca caaccctgtt aagaccatca agacaaatgt     120
tattggtacc ctgaacatgc taggacttgc aaagagagtt ggagctagga ttttgttgac     180
atcaacctct gaagtttatg gtgatccact tgagcatcct caaactgagg cctactgggg     240
caatgttaac ccgattggtg ttaggagttg ttatgatgag ggtaagcgtg tagcagagac     300
attgatgttc gactatcaca ggcagcatgg cattgaaatc cggattgcca ggattttcaa     360
cacctacggg cctaggatga acattgatga tggccgtgtt gttagcaact tcattgctca     420
ggctgtgcgc ggtgagcccc tgactgtcca gaggccagga acacagacta ggagtttctg     480
ctatgttgcc gatatggttg atggtcttat taagctgatg aatggaaaca gcactggacc     540
gattaacttg gggaacccag gtgaattcac catgctggaa cttgctgaga atgtgaagga     600
gttgatcaac ccagatgtga cagtgacgat gaccgagaac actcctgatg accccgcca      660 gaggaagccg gacatcacaa aggcgaagga agttctggga tggagccca agatcgtcct     720 gcgggacggc ttggtgctca tggaggatga tttccgggag cgcctgaccg tgcccaagaa     780
aaccaaggcc tgaattgccc tgcagttggg gaagaatatc cacacggggg agcatactca     840
tagtcgggct cgtcattatt tgtgg                                          865
```

```
<210> SEQ ID NO 19
<211> LENGTH: 1037
<212> TYPE: DNA
<213> ORGANISM: Artificial Sequence
<220> FEATURE:
<223> OTHER INFORMATION: 2nd version of inverted repeat region of Zm
      UXS6

<400> SEQUENCE: 19
atggcgtccg agccacgcgg cacttcgtcg gcggcaaggt gccgctgggc ctcaagcgga      60
aggcgctccg cgtcctcgtc accggcggcg ccggcttcgt cggcagccac ctggtggacc     120
gcctcctcga gcgcggcgac agcgttatcg tcgtcgataa cttcttcacc ggccgcaagg     180
acaacgttct tcaccacctc aacgacccaa acttcgagat gatccgccac gatgtcgtcg     240
agcccatcct gctcgaggtc gaccagatct accacctcgc ctgcccggcg tcccccgtcc     300
actacaaata caaccccatc aagacaatca agaccaatgt ggttgggact ctgaacatgc     360
tcggattagc aaagaggatc aacgccaggt tcctcctcac cagtaccagt gaggtctatg     420
gtgatcctct ccagcacccg caggtggaga cttactgggg caatgtcaat cccatcggtg     480
tcaggagctg ttacgatgag ggcaagcgta cagctgaaac gttgaccatg gattaccacc     540
gtggtgccaa ccttgaggtt aggatcgcac gtatcttcaa tacatatggc cctcgcatgt     600
gcattgacga tggccgtgtt gtcagtaact ttgttgctca ggcactgagg aaggagccct     660
tgacggttta tggtgatgga aagcaaacca ggagtttcca atatgtttct gatctggttg     720
agggtctgat gaagctgatg gaaggcgagc atgtggggcc attcaacctg ggtaaccctg     780
gcgagttcac catgcttgag cttgccaagg ttgtccagga caccatcgac cccaacgcac     840
ggatcgagtt ccgcaagaac acccaggacg acccgcacaa gcgcaagccc gacatcagcc     900
gcgccaagga gttcctcggg tgggagccga agatccccct gcgtgagggc cttcccctca     960
tggtctccga cttccgcaag cgcatcttcg gcgaccaaga cgctgctgcc accaccaccg    1020
gaaaccagca aggttag                                                   1037
```

UDP-XYLOSE SYNTHASES (UXS) POLYNUCLEOTIDES, POLYPEPTIDES, AND USES THEREOF

CROSS-REFERENCE TO RELATED APPLICATIONS

This application claims priority to and the benefit of U.S. Provisional Application No. 60/755,253, filed Dec. 30, 2005, which is herein incorporated in its entirety by reference.

FIELD OF THE INVENTION

The present invention relates to methods and compositions for grain improvement and/or improved digestibility of transgenic plants. In certain embodiments, these plants can contain a UDP-xylose synthase (UXS) nucleic acid that inhibits arabinoxylan and/or hemicellulose production resulting in improved digestibility and/or ease of grain processing. In other embodiments, these plants can contain a UXS nucleic acid over-expressed to increase arabinoxylan and/or hemicellulose production resulting in, for example, harder pericarp when expressed in seed.

BACKGROUND OF THE INVENTION

Primary plant cell walls contain approximately 15-20% hemicellulose in the vegetative tissue and 40-60% in the grain.

Hemicellulose in monocot walls consists mainly of arabinoxylan (also referred to as glucurono-arabinoxylan or pentosans), a branched polymer consisting of a beta-gylosyl backbone decorated with arabinosyl and glucuronosyl residues. This polymer is often referred to as arabinoxylan because of the relatively low proportion of glucuronosyl residues. Carpita, N. C., "Structure and Biogenesis of the Cell Walls of Grasses" *Annual Review of Plant Physiol. and Plant Molecular Biology* 476:445-476 (1996).

Dicot cell walls contain xyloglucan as a major hemicellulosic polymer. Xyloglucan is also a branched polymer consisting of a linear beta-glycosyl backbone decorated with xylosyl residues, some of which are substituted with galactosyl residues.

Cell walls of corn grain constitute about 6-8% of the total dry weight of the seed. Whistler, R. L. et al, *Hemicelluloses In Industrial Gums: Polysaccharides and Their Derivatives*, San Diego: Academic Press, pp. 295-308 (1993). The grain cell wall contains 45-65% arabinoxylan, the remainder being mainly cellulose. Arabinoxylans are considered to be anti-nutritional components of animal feed because they can absorb large amounts of water. This leads to increased viscosity and possible sequestering of other digestible feed components, such as starch and polypeptides, away from digestive enzymes.

Arabinoxylans are known to lower the food conversion ratio (FCR) of animal feed. Studies where fungal xylanase were included in cereal-derived feed showed improved FCR and weight gain in broilers and pigs. Veldman and Vahl, H. A., "Xylanase in broiler diets with differences in characteristics and content of wheat", *British Poultry Science* 35:537-550 (1994). The observed improvement in FCR and weight gain was higher than expected from arabinoxylan breakdown and digestion alone. Thus, arabinoxylan appears to reduce the digestion of other feed components. An unresolved need exists for methods and compositions to reduce the concentration of arabinoxylan (and thus hemicellulose) in grain.

Cellulose microfibrils have the highest tensile strength of any of the other cell wall polymers. Increasing the cellulose/arabinoxylan ratio in the cell wall should lead to a harder pericarp and improved ability to handle the grain.

About 12% of the corn processed through wet-milling is fiber (see: Johnson L A, and Can J B (2003) *Wet milling: the basis of corn biorefineries*; in *Corn: Chemistry and Technology*. P J White and L A Johnson (eds). AACC, St. Paul, Minn. pp. 449-494). Of this 12%, approximately 4% is coarse fiber (mainly pericarp-derived) and the rest is fine fiber. While coarse fiber consists of approximately 9% starch, fine fiber can have up to 30% starch, constituting 2.5% of the total dry mass. The other major component of fine fiber is arabinoxylan, which makes up to 21 % of this fraction. Some starch can become intricately associated with arabinoxylan, making it difficult to extract during wet-milling. A need exists for a method to reduce the concentration of arabinoxylan (and thus hemicellulose) in grain to improve starch extractability.

DETAILED DESCRIPTION OF THE INVENTION

Definitions Terms that are not otherwise defined herein are used in accordance with their plain and ordinary meaning.

Units, prefixes, and symbols can be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

As used herein, "a" or "an" can mean one or more than one of an item.

"UXS polynucleotide" refers to a nucleic acid construct that comprises at least part or all of the UXS nucleic acid sequence, non-limiting examples of which are provided in SEQ ID NOs: 1, 3, 5, 7, 9, 11, 13, and 15. A "polynucleotide" can be single, double and/or triple stranded and can comprise part or all of a native or modified UXS nucleic acid sequence. A "polynucleotide" can be designed to produce an inhibitory RNA that decreases expression of the endogenous UXS sequences. A "polynucleotide" can be of any size, from a short oligonucleotide to a full length UXS gene. A UXS "polynucleotide" sequence can be in the sense or anti-sense orientation. A "polynucleotide" can be of genomic or cDNA sequence.

The present invention also provides isolated polynucleotide sequences comprising transcriptional units for gene over-expression and gene-suppression that have been used either as single units or in combination as multiple units to transform plant cells.

A "transgenic plant" is one that contains an introduced segment of nucleic acid, such as a UXS nucleic acid. The introduced nucleic acid can encode a native UXS polynucleotide sequence or a modified polynucleotide sequence of any length, up to a full-length sequence. Any method known in the art can be used to transform one or more plant cells and regenerate a transgenic plant.

As used herein "operably linked" refers to a functional linkage between a promoter and/or other regulatory element and a second nucleic acid sequence, wherein the promoter initiates and mediates transcription of the second sequence.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, the term "plant" includes reference to whole plants, plant organs (e.g., leaves, stems, roots, etc.), seeds and plant cells and progeny of same. "Plant cell", as used herein includes, without limitation, seeds, suspension cultures, embryos, meristematic regions, callus tissue, leaves, roots, shoots, gametophytes, sporophytes, pollen, and microspores. The class of plants which can be used in the claimed methods is generally as broad as the class of higher plants amenable to transformation techniques, including both monocotyledonous and dicotyledonous plants.

By "fragment" is intended a portion of the nucleotide sequence or a portion of the amino acid sequence and hence protein encoded thereby. Fragments of a nucleotide sequence can encode protein fragments that retain the biological activity of the native nucleic acid, i.e. "functional fragments".

Alternatively, fragments of a nucleotide sequence that can be useful as hybridization probes may not encode fragment proteins retaining biological activity. Thus, fragments of a nucleotide sequence are generally greater than 25, 50, 100, 150, 200, 250, 300, 350, 400, 450, 500, 600, or 700 nucleotides and up to and including the entire nucleotide sequence encoding the proteins of the invention. Generally the probes are less than 1000 nucleotides and often less than 500 nucleotides.

Similarly, fragments of a nucleotide sequence that are useful for generating cells, tissues or plants transiently or permanently suppressing a gene or genes may not encode fragment proteins retaining biological activity. Fragments may be in sense or antisense orientation, reverse orientation, complementary, or a combination thereof. Thus, for example, fragments of such nucleotide sequence may range from at least about 10 nucleotides, to greater than 25, 50, 100, 200, 300, 400, 500, 600, or 700 nucleotides and up to and including the full-length nucleotide sequence-encoding native UXS proteins.

By "variants" is intended substantially similar sequences. Generally, nucleic acid sequence variants of the invention will have at least 60%, 65%, 70%, 75%, 76%, 77%, 78%, 79%, 80%, 85%, 86%, 87%, 88%, 89%, 90%, 91%, 92%, 93%, 94%, 95%, 96%, 97%, 98% or 99% sequence identity to the native nucleotide sequence, wherein the % sequence identity is based on the entire sequence and is determined by GAP 10 analysis using default parameters. Generally, polypeptide sequence variants of the invention will have at least about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the native protein, wherein the % sequence identity is based on the entire sequence and is determined by GAP 10 analysis using default parameters. GAP uses the algorithm of Needleman and Wunsch (J. Mol. Biol. 48:443-453, 1970) to find the alignment of two complete sequences that maximizes the number of matches and minimizes the number of gaps.

As used herein "transformation" can include stable transformation and transient transformation. Unless otherwise stated, "transformation" refers to stable transformation.

As used herein "stable transformation" refers to the transfer of a nucleic acid fragment into a genome of a host organism (this includes both nuclear and organelle genomes) resulting in genetically stable inheritance. In addition to traditional methods, stable transformation includes the alteration of gene expression by any means including chimeraplasty or transposon insertion.

As used herein "transient transformation" refers to the transfer of a nucleic acid fragment or protein into the nucleus (or DNA-containing organelle) of a host organism resulting in gene expression without integration and stable inheritance.

As used herein, the term "co-suppression" is used to collectively designate gene silencing methods based on mechanisms involving the expression of antisense, sense RNA molecules, aberrant RNA molecules, double-stranded RNA molecules, micro RNA molecules and the like.

"Non-ruminant animal" means an animal with a simple stomach divided into the esophageal, cardia, fundus and pylorus regions. A non-ruminant animal additionally implies a species of animal without a functional rumen. A rumen is a section of the digestive system where feedstuff/food is soaked and subjected to digestion by microorganisms before passing on through the digestive tract. This phenomenon does not occur in a non-ruminant animal. The term non-ruminant animal includes but is not limited to humans, swine, poultry, cats and dogs.

UDP-Xylose Synthases (UXS) in Plants

UDP-xylose (Xyl) is an essential sugar donor for the synthesis of hemicellulose, glycoproteins and oligosaccharides. UDP-Xyl also feedback inhibits upstream enzymes. In plants, the major route by which UDP-Xyl is produced is via UDP-Glucose. The biosynthesis of UDP-Xyl is catalyzed by different UDP-xylose synthase (UXS) isozymes, all of which convert UDP-GICA to UDP-Xyl by NADH dependent decarboxylation of UDP-glucuronic acid.

A plant UDP-xylose synthase (UXS) was purified from pea by peptide sequencing and enzyme activity was demonstrated with the recombinant polypeptide. The *A. thaliana* and rice genomes each contain six putative UXS genes that are highly similar to both the pea and fungal UXS genes. The subcellular location of UXS activities varies in different species. For example, the only UXS enzyme from rat is localized to the Golgi, while the sole UXS of *Cryptococcus* is cytosolic. In plants, activities of UXS enzymes are either soluble or membrane associated. Three of the *Arabidopsis* UXS isoforms (AtUXS 3, 5, 6) appear to be cytosolic and the other three (AtUxs 1, 2, 4) are likely to reside in the endomembrane system. In addition to six UXS isoforms, two *A. thaliana* genes that are distantly related to the UXS gene family apparently encode UDP-D-apiose/UDP-D-xylose synthase (AXS). Purified recombinant AXS1 generates UDP-D-xylose and UDP-D-apiose using UDP-D-glucuronic acid as its exclusive substrate.

Nucleic Acids

In various embodiments, nucleic acids of the invention can encode a UXS polypeptide sequence, an inhibitory RNA, or another type of UXS macromolecule. The nucleic acid can be derived from genomic DNA, complementary DNA (cDNA), RNA, or synthetic DNA. Where incorporation into an expression cassette is desired, the nucleic acid can also comprise one or more introns.

A nucleic acid includes single-stranded and double-stranded or triple-stranded molecules, as well as DNA, RNA, chemically modified nucleic acids and nucleic acid analogs. It is contemplated that a nucleic acid can be of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater nucleotide residues in length, up to a full length UXS gene.

UXS polypeptides can be encoded by any nucleic acid sequence that encodes the appropriate amino acid sequence. The design and production of nucleic acids encoding a desired amino acid sequence is well known to those of skill in the art, using standardized codon tables (see Table 1 below). The codons selected for encoding each amino acid can be modified to optimize expression of the nucleic acid in the host cell of interest, for example by using codons optimized for expression in maize. Codon preferences for various species of host cell are well known in the art.

TABLE 1

| Amino Acid | | Codons |
|---|---|---|
| Alanine | Ala | GCA GCC GCG GCU |
| Cysteine | Cys | UGC UGU |
| Aspartic acid | Asp | GAc GAU |
| Glutamic acid | Glu | GAA GAG |
| Phenylalanine | Phe | UUC UUU |
| Glycine | Gly | GGA GGC GGG GGU |
| Histidine | His | CAC CAU |
| Isoleucine | Ile | AUA AUC AUU |
| Lysine | Lys | AAA AAG |
| Leucine | Leu | UUA UUG CUA CUC CUG CUU |
| Methionine | Met | AUG |
| Asparagine | Asn | AAC AAU |
| Proline | Pro | CCA CCC CCG CCU |
| Glutamine | Gln | CAA CAG |
| Arginine | Arg | AGA AGG CGA CGC CGG CGU |
| Serine | Ser | AGC AGU UCA UCC UCG UCU |
| Threonine | Thr | ACA ACC ACG ACU |
| Valine | Val | GUA GUC GUG GUU |
| Tryptophan | Trp | UGG |
| Tyrosine | Ty | UAC UAU |

Nucleic Acids

Isolated nucleic acids can be made by any method known in the art, for example using standard recombinant methods, synthetic techniques, or combinations thereof. In some embodiments, the nucleic acids can be cloned, amplified, or otherwise constructed.

The nucleic acids can conveniently comprise sequences in addition to UXS nucleic acid sequences. For example, a multi-cloning site comprising one or more endonuclease restriction sites can be added. Regulatory sequences can be added to promote expression of the nucleic acid. Translatable sequences can be inserted to aid in the isolation of expressed polypeptides. For example, a hexa-histidine marker sequence provides a convenient means to purify tagged polypeptides. A nucleic acid can be attached to a cassette, adapter, or linker for cloning and/or expression of a nucleic acid. Additional sequences can be added to such cloning and/or expression sequences to optimize their function in cloning and/or expression, to aid in isolation of the nucleic acid, or to improve the introduction of the nucleic acid into a cell. Use of cloning cassettes, expression cassettes, adapters, and linkers is well known in the art.

Isolated nucleic acids, such as RNA, cDNA, genomic DNA, or a hybrid thereof, can be obtained from plant biological sources using any number of cloning methodologies known in the art. In some embodiments, oligonucleotide probes which selectively hybridize, under stringent conditions, to the nucleic acids are used to identify a sequence in a cDNA or genomic DNA library. Methods for isolation of mRNA and construction of cDNA and genomic libraries are known and any such known methods can be used. [See, e.g., Plant Molecular Biology: A Laboratory Manual, Clark, Ed., Springer-Verlag, Berlin (1997); Current Protocols in Molecular Biology, Ausubel, et al., Eds., Greene Publishing and Wiley-Interscience, New York (1995); Carninci et al., Genomics, 37:327-336 (1996); Ko, Nucl. Acids. Res., 18(19):5705-5711 (1990); Sambrook, et al., Molecular Cloning: A Laboratory Manual, 2nd Ed., Cold Spring Harbor Laboratory Vols. 1-3 (1989); Methods in Enzymology, Vol. 152, Guide to Molecular Cloning Techniques, Berger and Kimmel, Eds., San Diego: Academic Press, Inc. (1987).]

cDNA or genomic libraries, transgenic cell lines, transgenic plants or tissues or native plants or tissues can be screened for the presence and/or expression levels of UXS nucleic acids using a probe based upon one or more UXS sequences, such as those disclosed in the present invention. Probes also can be used to hybridize with genomic DNA or cDNA sequences to isolate homologous genes in the same or different plant species. Various degrees of stringency of hybridization can be employed in the assay. As the conditions for hybridization become more stringent, there must be a greater degree of complementarity between the probe and the target for duplex formation to occur. The degree of stringency can be controlled by temperature, ionic strength, pH and/or the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, minor sequence variations in the probes and primers can be compensated for by reducing the stringency of the hybridization and/or wash medium.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide.

Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. Exemplary moderate stringency conditions include hybridization in 40 to 45% formamide, 1 M NaCl, 1%

SDS at 37° C., and a wash in 0.5× to 1×SSC at 55° C. Exemplary high stringency conditions include hybridization in 50% formamide, 1 M NaCl, 1% SDS at 37° C., and a wash in 0.1×SSC at 60° C. Typically the time of hybridization is from 4 to 16 hours.

An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel et al., Eds., Greene Publishing and Wiley-Interscience, New York (1995). Often, cDNA libraries will be normalized to increase the representation of relatively rare cDNAs.

Nucleic acids of interest can also be amplified using a variety of known amplification techniques. For instance, polymerase chain reaction (PCR) technology can be used to amplify target sequences directly from genomic DNA or cDNA sequences. PCR and other in vitro amplification methods can also be useful, for example, to clone nucleic acid sequences that code for polypeptides to be expressed, to make nucleic acids to use as probes for detecting the presence of the desired mRNA in samples, for nucleic acid sequencing, or for other purposes. Examples of techniques of use for nucleic acid amplification are found in Berger, Sambrook, and Ausubel, as well as Mullis et al., U.S. Pat. No. 4,683,202 (1987); and, PCR Protocols A Guide to Methods and Applications, Innis et al., Eds., Academic Press Inc., San Diego, Calif. (1990). The T4 gene 32 polypeptide (Boehringer Mannheim) can be used to improve yield of long PCR products. PCR-based screening methods have been disclosed. [See, e.g., Wilfinger et al. BioTechniques, 22(3): 481-486 (1997).]

Isolated nucleic acids can be prepared by direct chemical synthesis by methods such as the phosphotriester method of Narang et al., Meth. Enzymol. 68:90-99 (1979); the phosphodiester method of Brown et al., Meth. Enzymol. 68:109-151 (1979); the diethylphosphoramidite method of Beaucage et al., Tetra. Lett. 22:859-1862 (1981); the solid phase phosphoramidite triester method of Beaucage and Caruthers, Tetra. Letts. 22(20):1859-1862 (1981), using an automated synthesizer as in Needham-VanDevanter et al., Nucleic Acids Res., 12:6159-6168 (1984); or by the solid support method of U.S. Pat. No. 4,458,066. Chemical synthesis generally produces a single stranded oligonucleotide. This can be converted into double stranded DNA by hybridization with a complementary sequence, or by polymerization with a DNA polymerase using the single strand as a template. While chemical synthesis of DNA is best employed for sequences of about 100 bases or less, longer sequences can be obtained by the ligation of shorter sequences.

A variety of cross-linking agents, alkylating agents and radical generating species can be used to bind, label, detect, and/or cleave nucleic acids. For example, Vlassov, V. V., et al., Nucleic Acids Res (1986) 14:4065-4076, disclose covalent bonding of a single-stranded DNA fragment with alkylating derivatives of nucleotides complementary to target sequences. A report of similar work by the same group is that by Knorre, D. G., et al., Biochimie (1985) 67:785-789. Iverson and Dervan also showed sequence-specific cleavage of single-stranded DNA mediated by incorporation of a modified nucleotide which was capable of activating cleavage (J Am Chem Soc (1987) 109:1241-1243). Meyer, R. B., et al., J Am Chem Soc (1989) 111:8517-8519 disclose covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., Biochemistry (1988) 27:3197-3203. Use of crosslinking in triple-helix forming probes was also disclosed by Horne, et al., J Am Chem Soc (1990) 112:2435-2437. Use of N4, N4-ethanocytosine as an alkylating agent to crosslink to single-stranded oligonucleotides has also been disclosed by Webb and Matteucci, J Am Chem Soc (1986) 108:2764-2765; Nucleic Acids Res (1986) 14:7661-7674; Feteritz et al., J. Am. Chem. Soc. 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Expression Cassettes

Various embodiments concern cassettes comprising UXS nucleic acids, which cassettes can be transformed into a target host cell. An expression cassette will typically comprise a nucleic acid operably linked to transcriptional regulatory elements which will direct the transcription of the nucleic acid. For example, plant expression cassettes can include a cloned UXS nucleic acid under the transcriptional control of 5' and 3' regulatory sequences. Expression cassettes can contain a promoter sequence (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

The nucleotide sequences for use in the methods of the present invention are provided in expression cassettes for transcription in the plant of interest. Such expression cassettes are provided with a plurality of restriction sites for insertion of any sequence of the present invention to be placed under the transcriptional regulation of the regulatory regions. The expression cassettes may additionally contain selectable marker genes.

The expression cassette can include in the 5'-3' direction of transcription, a transcriptional and translational initiation region, any seed protein sequence of the invention, and optionally, a transcriptional and translational termination region functional in plants. The transcriptional initiation region, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a gene comprises a coding sequence operably linked to a transcription initiation region that is heterologous to the coding sequence. Alternatively, a gene comprises fragments of at least two independent transcripts that are linked in a single transcription unit.

While it may be preferable to express the sequences using heterologous promoters, the native promoter sequences may be used. Such constructs would alter expression levels of the proteins in the plant or plant cell. Thus, the phenotype of the plant or plant cell is altered. Alternatively, the promoter sequence may be used to alter expression. For example, the promoter (or fragments thereof) of a UXS sequence of the present invention can modulate expression of the native UXS protein or other closely related proteins.

Use of a termination region is not necessary for proper transcription of plant genes but may be used as part of an expression construct. The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; and Joshi et al. (1987) Nucleic Acid Res. 15:9627-9639.

Where appropriate, the genes can be synthesized using plant-preferred codons for improved expression. See, for example, Campbell and Gowri (1990) Plant Physiol. 92:1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. Sci. USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, N.Y.), pp. 237-256); and maize chlorotic mottle virus leader (MCMV) (Lommel et al. (1991) Virology 81:382-385). See also, Della-Cioppa et al. (1987) Plant Physiol. 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christopherson et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 49:603-612; Figge et al. (1988) Cell 52:713-722; Deuschle et al. (1989) Proc. Natl. Acad. Aci. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90:1917-1921; Labow et al. (1990) Mol. Cell. Biol. 10:3343-3356; Zambretti et al. (1992) Proc. Natl. Acad. Sci. USA 89:3952-3956; Baim et al. (1991) Proc. Natl. Acad. Sci. USA 88:5072-5076; Wyborski et al. (1991) Nucleic Acids Res. 19:4647-4653; Hillenand-Wissman (1989) Topics Mol. Struc. Biol. 10:143-162; Degenkolb et al. (1991) Antimicrob. Agents Chemother. 35:1591-1595; Kleinschnidt et al. (1988) Biochemistry 27:1094-1104; Bonin (1993) Ph.D. Thesis, University of Heidelberg; Gossen et al. (1992) Proc. Natl. Acad. Sci. USA 89:5547-5551; Oliva et al. (1992) Antimicrob. Agents Chemother. 36:913-919; Hlavka et al. (1985) Handbook of Experimental Pharmacology, Vol. 78 ( Springer-Verlag, Berlin); Gill et al. (1988) Nature 334:721-724. Such disclosures are herein incorporated by reference.

The above list of selectable marker genes is not meant to be limiting. Any selectable marker gene can be used in the present invention.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) Proc. Natl. Acad. Sci. USA 96:8774-8778; herein incorporated by reference.

A number of promoters can be used in the practice of the invention. The promoters can be selected based on the desired outcome. The nucleic acids can be combined with constitutive, tissue-preferred, or other promoters for expression in plants, more preferably a promoter functional during seed development.

Such constitutive promoters include, for example, the core promoter of the Rsyn7 promoter and other constitutive promoters disclosed in WO 99/43838; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible and tetracycline-repressible promoters (see, for example, Gatz et al. (1991) Mol. Gen. Genet. 227:229-237, and U.S. Pat. Nos. 5,814,618 and 5,789,156), herein incorporated by reference.

Tissue-preferred promoters can be utilized to target enhanced protein expression within a particular plant tissue. Tissue-preferred promoters include, but are not limited to: Yamamoto et al. (1997) Plant J. 12(2)255-265; Kawamata et al. (1997) Plant Cell Physiol. 38(7):792-803; Hansen et al. (1997) Mol. Gen Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol Biol. 23(6): 1129-1138; Matsuoka et al. (1993) Proc Natl. Acad. Sci. USA 90(20):9586-9590; and Guevara-Garcia et al. (1993) Plant J. 4(3):495-505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10:108, herein incorporated by reference. Such seed-preferred promoters include, but are not limited to, Cim1 (cytokinin-induced message); cZ19B1 (maize 19 kD zein); and milps (myo-inositol-1-phosphate synthase; see U.S. Pat. No 6,225, 529 herein incorporated by reference). The 27 kD gamma-zein is a preferred endosperm-specific promoter. Glb-1 is a preferred embryo-specific promoter.

For dicots, seed-specific promoters include, but are not limited to, bean β-phaseolin, napin, β-conglycinin, soybean lectin, cruciferin, and the like.

For monocots, seed-specific promoters include, but are not limited to, maize 15 kD zein, 22 kD zein, 27 kD zein, 10 kD delta-zein, waxy, shrunken 1, shrunken 2, globulin 1, etc.

Regulation of Gene Expression

While not critical to the invention, the methods of the invention comprise either increasing or decreasing the level of a target gene product. Methods for inhibiting gene expression are well known in the art. Although any method know in the art for reducing the level of protein in a plant could be used, possible methods for reducing protein include, but are not limited to, homology-dependent gene silencing, antisense technology, co-suppression including, for example, RNA interference (RNAi), micro RNA and the like, site-specific recombination, site-specific integration, mutagenesis including transposon tagging, and biosynthetic competition, homologous recombination, and gene targeting, alone or in combination. Depending upon the intended goal, the level of at least one seed protein may be increased, decreased, or eliminated.

Catalytic RNA molecules or ribozymes may also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is disclosed, for example, in Haseloff et al., *Nature* 334:585-591 (1988).

A "co-suppression" cassette may include 5' (but not necessarily 3') regulatory sequences, operably linked to at least one of the sequences of the invention. Co-suppression cassettes used in the methods of the invention can comprise sequences of the invention in so-called "inverted repeat" structures. The cassette may additionally contain a second copy of the fragment in opposite direction to form an inverted repeat structure: opposing arms of the structure may or may not be interrupted by any nucleotide sequence related or unrelated to the nucleotide sequences of the invention. (see Fiers et al. U.S. Pat. No. 6,506,559). The transcriptional units are linked to be co-transformed into the organism. Alternatively, additional transcriptional units can be provided on multiple over-expression and co-suppression cassettes.

The methods of transgenic co-suppression can be used to reduce or eliminate the level of at least one seed protein in grain. One method of transgenic co-suppression comprise transforming a plant cell with at least one transcriptional unit containing an expression cassette comprising a promoter that drives transcription in the plant operably linked to at least one nucleotide sequence transcript in the sense orientation encoding at least a portion of the seed protein of interest. Methods for suppressing gene expression in plants using nucleotide sequences in the sense orientation are known in the art. The methods generally involve transforming plants with a DNA construct comprising a promoter that drives transcription in a plant operably linked to at least a portion of a nucleotide sequence that corresponds to the transcript of the endogenous gene. Typically, such a nucleotide sequence has substantial sequence identity to the sequence of the transcript of the endogenous gene, at least about 65%, 70%, 75%, 80%, 85%, 90%, 91%, 92%, 93%, 94%, 95%, 96%, 97%, 98%, or 99% or more sequence identity over the entire length of the sequence. Furthermore, portions, rather than the entire nucleotide sequence, of the polynucleotides may be used to disrupt the expression of the target gene product. Generally, sequences of at least 10, 15, 20, 21, 22, 23, 24, 25, 26, 27, 28, 29, 30, 35, 40, 45, 50, 55, 60, 65, 70, 75, 80, 85, 90, 95, 100, 200 nucleotides, or greater may be used. See U.S. Pat. Nos. 5,283,184 and 5,034,323; herein incorporated by reference.

The endogenous gene targeted for co-suppression may be a gene encoding any seed protein that accumulates as a seed protein in the plant species of interest, including, but not limited to, the seed genes noted above. For example, where the endogenous gene targeted for co-suppression is a UXS gene disclosed herein, co-suppression is achieved using an expression cassette comprising a UXS gene sequence, or variant or fragment thereof.

Additional methods of co-suppression are known in the art and can be similarly applied to the instant invention. These methods involve the silencing of a targeted gene by spliced hairpin RNA's and similar methods also called RNA interference and promoter silencing (see Smith et al. (2000) Nature 407:319-320, Waterhouse and Helliwell (2003)) Nat. Rev. Genet. 4:29-38; Waterhouse et al. (1998) Proc. Natl. Acad. Sci. USA 95:13959-13964; Chuang and Meyerowitz (2000) Proc. Natl. Acad. Sci. USA 97:4985-4990; Stoutjesdijk et al. (2002) Plant Phystiol. 129:1723-1731; and Patent Application WO 99/53050; WO 99/49029; WO 99/61631; WO 00/49035 and U.S. Pat. No. 6,506,559, each of which is herein incorporated by reference). For the purpose of this invention the term "co-suppression" is used to collectively designate gene silencing methods based on mechanisms involving the expression of sense RNA molecules, aberrant RNA molecules, double-stranded RNA molecules, micro RNA molecules and the like.

The expression cassette for co-suppression may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, International Publication No. WO 02/00904, herein incorporated by reference.

In other embodiments of the invention, inhibition of the expression of a protein of interest may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier et al. (2003) Nature 425: 257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). miRNA molecules are highly efficient at inhibiting the expression of endogenous genes, and the RNA interference they induce is inherited by subsequent generations of plants In one embodiment, the polynucleotide to be introduced into the plant comprises an inhibitory sequence that encodes a zinc finger protein that binds to a gene encoding a protein of the invention resulting in reduced expression of the gene. In particular embodiments, the zinc finger protein binds to a regulatory region of a UXS gene. In other embodiments, the zinc finger protein binds to a messenger RNA encoding a seed protein and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 20030037355; each of which is herein incorporated by reference.

Methods for antisense suppression can be used to reduce or eliminate the level of at least one protein of the invention. The methods of antisense suppression comprise transforming a plant cell with at least one expression cassette comprising a promoter that drives expression in the plant cell operably linked to at least one nucleotide sequence that is antisense to a nucleotide sequence transcript of the target protein. By "antisense suppression" is intended the use of nucleotide sequences that are antisense to nucleotide sequence transcripts of endogenous plant genes to suppress the expression of those genes in the plant.

Methods for suppressing gene expression in plants using nucleotide sequences in the antisense orientation are known in the art. The methods generally involve transforming plants with a DNA construct comprising a promoter that drives expression in a plant operably linked to at least a portion of a nucleotide sequence that is antisense to the transcript of the endogenous gene. Antisense nucleotides are constructed to hybridize with the corresponding mRNA. Modifications of the antisense sequences may be made as long as the sequences hybridize to and interfere with expression of the corresponding mRNA. In this manner, antisense constructions having at least about 70%, 75%, 80%, 85%, 90%, 91%, 92%, 93%, 94%, 95%, 96%, 97%, 98%, or 99% or more sequence identity to the corresponding antisense sequences may be used. Furthermore, portions, rather than the entire nucleotide sequence, of the antisense nucleotides may be used to disrupt the expression of the target gene. Generally, sequences of at least 10 nucleotides, 50 nucleotides, 100 nucleotides, 200 nucleotides, or greater may be used.

Methods for transposon tagging can be used to reduce or eliminate the level of at least one seed protein in grain. The methods of transposon tagging comprise insertion of a transposon within an endogenous plant seed gene to reduce or eliminate expression of the seed protein.

Methods for transposon tagging of specific genes in plants are well known in the art (see for example, Maes et al. (1999) Trends Plant Sci. 4:90-96; Dharmapuri and Sonti (1999) FEMS Microbiol. Lett. 179:53-59; Meissner et al. (2000)

Plant J. 22:265-274; Phogat et al. (2000) J. Biosci. 25:57-63; Walbot (2000) Curr. Opin. Plant Biol. 2:103-107; Gai et al. (2000) Nuc. Acids Res. 28:94-96; Fitzmaurice et al. (1999) Genetics 153:1919-1928). In addition, the TUSC process for selecting Mu insertions in selected genes has been described (Bensen et al. (1995) Plant Cell 7:75-84; Mena et al. (1996) Science 274:1537-1540; U.S. Pat. No. 5,962,764, which is herein incorporated by reference).

Other methods for inhibiting or eliminating the expression of endogenous genes are also known in the art and can be similarly applied to the instant invention. These methods include other forms of mutagenesis, such as ethyl methane-sulfonate-induced mutagenesis, deletion mutagenesis, and fast neutron deletion mutagenesis used in a reverse genetics sense (with PCR) to identify plant lines in which the endogenous gene has been deleted (for examples of these methods see Ohshima et al. (1998) Virology 243:472-481; Okubara et al. (1994) Genetics 137:867-874; Quesada et al. (2000) Genetics 154:421-436. In addition, a fast and automatable method for screening for chemically induced mutations, TILLING, (Targeting Induced Local Lesions In Genomes), using a denaturing HPLC or selective endonuclease digestion of selected PCR products is also applicable to the instant invention (see McCallum et al. (2000) Nat. Biotechnol. 18:455-457).

Mutation breeding is another of many methods that could be used to introduce new traits into an elite line. Mutations that occur spontaneously or are artificially induced can be useful sources of variability for a plant breeder. The goal of induced mutagenesis is to increase the rate of mutation for a desired characteristic. Mutation rates can be increased b many different means including: temperature; long-term seed storage; tissue culture conditions; radiation such as X-rays, Gamma rays (e.g., Cobalt 60 or Cesium 137), neutrons, (product of nuclear fission by Uranium 235 in an atomic reactor, Beta radiation (emitted from radioisotopes such as P32, or C14), or ultraviolet radiation (preferably from 2500 to 2900 nm); or chemical mutagens such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis, the trait may then be incorporated into existing germplasm by traditional breeding techniques, such as back-crossing. Details of mutation breeding can be found in "Principals of Cultivar Development" Fehr, 1993 (Macmillan Publishing Company), the disclosures of which are incorporated herein by reference. In addition, mutations created in other lines may be used to produce a backcross conversion of elite lines that comprise such mutations.

Other methods for inhibiting or eliminating the expression of genes include the transgenic application of transcription factors (Pabo, C. O., et al. (2001) Annu Rev Biochem 70, 313-40.; and Reynolds, L., et al (2003), Proc Natl Acad Sci U S A 100, 1615-20.), and homologous recombination methods for gene targeting (see U.S. Pat. No. 6,187,994).

Similarly, it is possible to eliminate the expression of a single gene by replacing its coding sequence with the coding sequence of a second gene using homologous recombination technologies (see Bolon, B. Basic Clin. Pharmacol. Toxicol. 95:4, 12, 154-61 (2004); Matsuda and Alba, A., Methods Mol. Bio. 259:379-90 (2004); Forlino, et. al., J. Biol. Chem. 274:53, 37923-30 (1999)). For example, by using the knock-out/knock-in technology, the coding sequence of a UXS polypeptide can be replaced by the coding sequence of a closely related polypeptide resulting in suppression of UXS protein expression and in over-expression of the closely related protein.

In some embodiments, the polynucleotide expressed by the expression cassette of the invention is catalytic RNA or has ribozyme activity specific for the messenger RNA of a protein of interest. Thus, the polynucleotide causes the degradation of the endogenous messenger RNA, resulting in reduced expression of one or more proteins. This method is described, for example, in U.S. Pat. No. 4,987,071, herein incorporated by reference.

In some embodiments of the invention, the polynucleotide comprises an inhibitory sequence that encodes an antibody that binds to at least one isoform of a seed protein, and reduces the level of the seed protein. In another embodiment, the binding of the antibody results in increased turnover of the antibody-antigen complex by cellular quality control mechanisms. The expression of antibodies in plant cells and the inhibition of molecular pathways by expression and binding of antibodies to proteins in plant cells are well known in the art. See, for example, Conrad and Sonnewald (2003) *Nature Biotech.* 21:35-36, incorporated herein by reference.

Plant transformants containing a desired genetic modification as a result of any of the above described methods resulting in increased, decreased or eliminated expression of the seed protein of the invention can be selected by various methods known in the art. These methods include, but are not limited to, methods such as SDS-PAGE analysis, immunoblotting using antibodies which bind to the seed protein of interest, single nucleotide polymorphism (SNP) analysis, or assaying for the products of a reporter or marker gene, and the like.

Plant Cell Transformation

Transformation protocols as well as protocols for introducing nucleotide sequences into plants can vary depending on the type of plant or plant cell, i.e., monocot or dicot, targeted for transformation. Suitable methods of introducing nucleotide sequences into plant cells and subsequent insertion into the plant genome include, but are not limited to: microinjection (Crossway et al. (1986) Biotechniques 4:320-334); electroporation (Riggs et al. (1986) Proc. Natl. Acad. Sci. USA 83:5602-5606); *Agrobacterium*-mediated transformation (Townsend et al., U.S. Pat. No. 5,563,055; Zhao et al., U.S. Pat. No. 5,981,840; Cai et al., U.S. patent application Ser. No. 09/056,418); direct gene transfer (Paszkowski et al. (1984) EMBO J. 3:2717-2722); and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al. (1988) Biotechnology 6:923-926). Also see Weissinger et al. (1988) Ann. Rev. Genet. 22:421-477; Sanford et al. (1987) Particulate Science and Technology 5:27-37 (onion); Christou et al. (1988) Plant Physiol. 87:671-674 (soybean); McCabe et al. (1988) Bio/Technology 6:923-926 (soybean); Finer and McMullen (1991) In Vitro Cell Dev. Biol. 27P:175-182 (soybean); Singh et al. (1998) Theor. Appl. Genet. 96:319-324 (soybean); Datta et al. (1990) Biotechnology 8:736-740 (rice); Klein et al. (1988) Proc. Natl. Acad. Sci. USA 85:4305-4309 (maize); Klein et al. (1988) Biotechnology 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) Plant Physiol. 91:440-444 (maize); Fromm et al. (1990) Biotechnology 8:833-839 (maize); Hooykaas-Van Slogteren et al. (1984) Nature (London) 311:763-764; Bowen et al., U.S. Pat. No. 5,736,369 (cereals); Bytebier et al. (1987) Proc. Natl. Acad. Sci. USA 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505 (electroporation); Li et al. (1993) Plant Cell Reports 12:250-255 and Christou and Ford (1995) Annals of Botany 75:407-413 (rice); Osjoda et al. (1996) Nature Biotechnology 14:745-750 (maize via *Agrobacterium tumefaciens*); all of which are herein incorporated by reference.

The methods of the invention can involve introducing a nucleotide construct into a plant. By "introducing" is intended presenting to the plant the nucleotide construct in such a manner that the construct gains access to the interior of a cell of the plant. The claimed methods do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the protein of interest of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

Other methods of transformation include *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) discloses the use of *A. rhizogenes* strain A4 and its Ri plasmid along with *A. tumefaciens* vectors pARC8 or pARC16

The introduction of DNA constructs using PEG precipitation is disclosed in Paszkowski et al., EMBO J. 3: 2717-2722 (1984). Electroporation techniques are disclosed in Fromm et al., Proc. Natl. Acad. Sci. (USA) 82: 5824 (1985). Ballistic transformation techniques are disclosed in Klein et al., Nature 327:70-73 (1987). Alternative transformation methods include liposome-mediated DNA uptake (see, e.g., Freeman et al., Plant Cell Physiol. 25: 353 (1984)) and the vortexing method (see, e.g., Kindle, Proc. Natl. Acad. Sci., (USA) 87:1228 (1990)).

DNA can also be introduced into plants by direct DNA transfer into pollen as disclosed by Zhou et al., Methods in Enzymology, 101:433 (1983); D. Hess, Intern Rev. Cytol., 107:367 (1987); Luo et al., Plant Mol. Biol. Reporter, 6:165 (1988). Expression of polypeptide coding genes can be obtained by injection of the DNA into reproductive organs of a plant as disclosed by Pena et al., Nature, 325:274 (1987). DNA can also be injected directly into the cells of immature embryos and the rehydration of desiccated embryos as disclosed by Neuhaus et al., Theor. Appl. Genet., 75:30 (1987); and Benbrook et al., in Proceedings Bio Expo 1986, Butterworth, Stoneham, Mass., pp. 27-54 (1986). A variety of plant viruses that can be employed as vectors are known in the art and include cauliflower mosaic virus (CaMV), geminivirus, brome mosaic virus, and tobacco mosaic virus. The claimed methods and compositions are not limiting as to the method of transformation and any such plant transformation method known in the art can be utilized.

Transgenic Plant Regeneration

Transformed plant cells which are derived by any of the above transformation techniques can be cultured to regenerate a whole plant which possesses the transformed genotype and/or phenotype. See, for example, McCormick et al. (1986) Plant Cell Reports 5:81-84, incorporated herein by reference. These plants can then be grown, and either pollinated with the same transformed strain or different strains, and the resulting hybrid having expression of the desired phenotypic characteristic identified. Two or more generations can be grown to ensure that expression of the desired phenotypic characteristic is stably maintained and inherited and then seeds harvested to ensure expression of the desired phenotypic characteristic has been achieved.

Plants cells transformed with a plant expression cassette can be regenerated, e.g., from single cells, callus tissue or leaf discs according to standard plant tissue culture techniques. Various cells, tissues, and organs can be successfully cultured to regenerate an entire plant. Plant regeneration from cultured protoplasts is disclosed in Evans et al., Protoplasts Isolation and Culture, Handbook of Plant Cell Culture, Macmillan Publishing Company, New York, pp. 124-176 (1983); and Binding, Regeneration of Plants, Plant Protoplasts, CRC Press, Boca Raton, pp. 21-73 (1985).

The regeneration of plants containing a foreign gene introduced by *Agrobacterium* from leaf explants can be achieved as disclosed by Horsch et al., Science, 227:1229-1231 (1985). In this procedure, transformants are grown in the presence of a selection agent and in a medium that induces the regeneration of shoots in the plant species being transformed. These transformed shoots are then transferred to an appropriate root-inducing medium containing a selective agent and an antibiotic to prevent bacterial growth.

Regeneration can also be obtained from plant callus, explants, organs, or parts thereof. The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, The Maize Handbook, Freeling and Walbot, Eds., Springer, N.Y. (1994); Corn and Corn Improvement, 3rd edition, Sprague and Dudley Eds., American Society of Agronomy, Madison, Wis. (1988).

The desired genetically altered trait can be bred into other plant lines possessing desirable agronomic characteristics using conventional breeding methods and/or top-cross technology. The top-cross method is taught in U.S. Pat. No. 5,704,160 herein incorporated in its entirety by reference.

Methods for cross pollinating plants are well known to those skilled in the art, and are generally accomplished by allowing the pollen of one plant, the pollen donor, to pollinate a flower of a second plant, the pollen recipient, and then allowing the fertilized eggs in the pollinated flower to mature into seeds. Progeny containing the entire complement of heterologous coding sequences of the two parental plants can be selected from all of the progeny by standard methods available in the art for selecting transformed plants. If necessary, the selected progeny can be used as either the pollen donor or pollen recipient in a subsequent cross pollination.

Parts obtained from the regenerated plant, such as flowers, seeds, leaves, branches, fruit, and the like are included in the claimed methods and compositions, provided that these parts comprise cells comprising the disclosed nucleic acids of the invention. Progeny and variants and mutants of the regenerated plants are also included within the scope of the claimed subject matter, provided that these parts comprise the introduced nucleic acid sequences.

Transgenic plants expressing a selectable marker can be screened for transmission of one or more target nucleic acids by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can be analyzed for polypeptide expression by Western immunoblot analysis using specifically or selectively reactive antibodies. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

The claimed methods and/or compositions further provides for modulating (i.e., increasing or decreasing) the concentration or ratio of polypeptides, such as UXS polypeptides, in a plant or part thereof. Modulation can be effected by increasing or decreasing the concentration and/or the ratio of the polypeptides in a plant.

EXAMPLES

The following examples are included to illustrate various embodiments of the invention. It should be appreciated by those of skill in the art that the techniques disclosed in the examples which follow represent techniques discovered to function well in the practice of the claimed methods. However, those of skill in the art should, in light of the present disclosure, appreciate that many changes can be made in the specific embodiments which are disclosed and still obtain a like or similar result without departing from the spirit and scope of the invention.

Example 1

UDP-Xylose Synthase Isoforms

Eight UXS isoforms were identified and named UXS1 through 8. Amino acid sequences of the maize isoforms are provided in the sequence listing as SEQ ID NOS: 2, 4, 6, 8, 10, 12, 14, and 16. Nucleic acid sequences encoding the UXS isoforms are provided in the sequence listing as SEQ ID NOS: 1, 3, 5, 7, 9, 11, 13, and 15. The eight isoforms can be generally classified into three distinct types. Type A includes ZmUXS1 and 2, orthologous to AtUXS3, 5, 6, which are likely soluble and cytosolic localized. Type B includes ZmUXS3 and 4, orthologous to AtUXS1. Type C includes ZmUXS5, 6, 7, and 8, orthologous to AtUXS2 and 4. Both type B and C contain a trans-membrane domain and are likely Golgi localized.

Expression levels of different UXS isoforms were determined in different maize tissues using standard techniques. Briefly, the eight UXS DNA sequences were used to blast an MPSS tag library and unique tags were identified for each isoform (Massively Parallel Signature Sequencing) technology from LYNX™ (see Brenner et al, *Nature Biotechnology* 18:630-634 (2000). The unique and 3' most tags for each isoform were used to blast the MPSS profiling database. The average abundance of the tags was calculated from LYNX libraries for each tissue, with the expression levels of the UXS isoforms taken from the relative abundance of the corresponding tags.

UXS expression in maize endosperm showed a different developmental pattern from other seed tissues, with a decrease in total UXS expression observed between 6 DAP (days after pollination) and 40 DAP. The isoform profile shifted from primarily zmUXS1, zmUXS2 and zmUXS6 at DAP6 to an almost equal, but low, mixture of isoforms 1, 2, 3, 4, 6 and 8 at DAP 40.

In contrast, maize pericarp showed an increase in total UXS expression from DAP 5 to DAP 27. However the dominant isoforms in pericarp did not vary much with time after pollination, being primarily zmUXS1 and zmUXS2, with a lesser amount of zmUXS6 at DAP 5. Although the total expression level increases at DAP 27, the same three isoforms predominated. A comparison of various maize tissues showed that zmUXS1, zmUXS2 and zmUXS6 tended to be the predominant isoforms expressed in maize, although the relative levels varied from tissue to tissue. ZmUXS3, zmUXS4 and zmUXS8 appear to be minor alleles in general in maize.

Example 2

*Agrobacterium*-Mediated Transformation of Maize

For *Agrobacterium*-mediated transformation of maize, nucleotide sequences of interest such as UXS sequences were operably linked to a promoter as disclosed below employing the transformation method of Zhao et al (U.S. Pat. No. 5,981,840, and PCT patent publication WO98/32326; the contents of which are hereby incorporated by reference). Briefly, immature embryos were isolated from maize and the embryos contacted with a suspension of *Agrobacterium*, where the bacteria were capable of transferring the nucleotide sequence of interest to at least one cell of at least one of the immature embryos (infection). In this step the immature embryos were immersed in an *Agrobacterium* suspension for the initiation of inoculation. The embryos were co-cultured for a time with the *Agrobacterium* (co-cultivation). The immature embryos were cultured on solid medium following infection. Following this co-cultivation period an optional "resting" stage was performed. In this resting stage, the embryos were incubated in the presence of at least one antibiotic known to inhibit the growth of *Agrobacterium* without the addition of a selective agent for plant transformants (resting). The immature embryos were cultured on solid medium with antibiotic, but without a selecting agent, for elimination of *Agrobacterium* and for a resting phase for the infected cells. Next, inoculated embryos were cultured on medium containing a selective agent and growing transformed callus was recovered (selection). The immature embryos were cultured on solid medium with a selective agent resulting in the selective growth of transformed cells. The callus was then regenerated into plants and calli grown on selective medium were cultured on solid medium to regenerate the plants.

Example 3

Analyzing Seed for Hemicellulose Content

For a given ear, dissected endosperms were pooled into wild type or transgenic based on Western blot results. The pooled endosperm tissue was ground and weighed out into samples in duplicate 2 ml screw top microfuge tubes for hemicellulose preparations.

Removal of Soluble Sugars:

Small stir bars were placed in each tube and 1 ml 80% ethanol added and vortexed to mix. Tubes were heated in heat block set at 100° C. for 30 seconds and again vortexed to mix.

Tubes were then centrifuged at 14,000 rpm for 10 minutes and the supernatant discarded using vacuum. 1 ml of acetone was added and tubes vortexed to mix.

After another centrifugation at 14,000 rpm for 10 minutes, supernatant was again discarded using vacuum and pellets left in hood to dry (about 4 hours).

De-Starching:

0.3 ml of α-amylase solution (300 U/assay amylase in MOP buffer) was added to the tubes and mixed by vortexing. Tubes were then placed in racks and immersed in hot water. Heating proceeded at 90-95° C. for 15 minutes with constant stirring on magnetic stir plate. Samples were cooled slightly and briefly spun down to remove moisture by centrifugation (1 minute). At this point, 0.2 ml of 285 mM Na-acetate containing AMG (20 U/assay) mix was added and tubes incubated at 55° C. for 4 hours or overnight followed by a brief spin down by centrifugation (1 minute) to remove moisture.

Washing:

1.25 ml of absolute ethanol was added to each tube (bringing final ethanol concentration to 70%). Samples were vortexed and cooled on ice or in −20 freezer for 10-15 minutes.

Three rounds of centrifugation at 14,000 rpm for 10 minutes after which the supernatant was discarded using vacuum and 1 ml 80% ethanol added and vortexed between rounds. After the last round of centrifugation, the supernatant was vacuum removed and discarded and 1 ml acetone added, vortexed, and centrifuged at 14,000 rpm for 10 minutes. This supernatant was also removed using vacuum and discarded. The pellets were then allowed to air-dry in fume hood.

Hydrolyzing and Quantifying Hemicellulose:

1 ml of 1 M $H_2SO_4$ was added to air-dried tubes and vortexed to mix. Samples were then heated in 100° C. heat block for 45 minutes and vortexed every few minutes to mix. Samples were then cooled on ice.

Samples were centrifuged at 14,000 rpm for 10 minutes and 0.6 ml of supernatant removed into new tubes for HPLC.

Sugar residues from hemicellulose were quantified by HPLC Dionex CarboPac PA-1, 4×250 mm analytical column, PN 35391 Dionex PAD, with pulsed amperometric detector.

Individual hemicellulosic sugar residue was expressed as percent of endosperm weight. Arabinoxylan is the sum of arabinose and xylose % of control e.g.: arabinoxylan (transgenic)/arabinoxylan (wild type)×100.

Example 4

Down-Regulation of UDP-Xylose Synthases in Grain to Reduce Hemicellulose

Based on expression profiles, members of Type A (ZmUXS1 and 2) and Type C (ZmUXS5, 6, 7, and 8) showed relatively high levels of expression in all three tissues of grain (pericarp, endosperm, and embryo), while members of Type B (ZmUXS3 and 4) had apparently low endogenous expression in grain. Because of the high degree of nucleotide sequence homology between UXS1 and 2 and between UXS5, 6, 7 and 8, RNAi constructs of UXS2 and UXS6 under the control of promoters specific for pericarp, endosperm, and embryo are expected to result in silencing expression of both groups of UXS isoforms. In turn, it is expected that a reduction of hemicellulose content in maize kernel will occur, improving grain digestibility and increasing efficiency of ethanol output per unit grain in dry milling.

As demonstrated in the case of UDP-GDH, (U.S. Pat. No. 6,399,859) a practical approach to reduce hemicellulose content can comprise blocking nucleotide sugar biosynthesis. UDP-xylose synthase (UXS) can also be used for this purpose because the reaction UXS catalyzes is downstream of UDP-GDH and additionally bypasses the myo-inositol pathway. Therefore, blocking UXS should provide potent and specific inhibition of hemicellulose production by inhibiting UDP-xylose synthesis.

The following constructs were prepared for co-suppression of UXS expression in maize. Promoters on each end of the expression cassette direct the insert to be expressed in different tissues at different times if desired. The cassettes contain no termination signals. The cassette included a selectable marker gene such as PAT (Wohlleben et al (1988) *Gene* 70:25-37, or BAR for resistance to Basta/phosphinothricin.

Methods of construction of such expression cassettes is well known to those of skill in the art in light of the present disclosure. See, for example, e.g., Sambrook et al. (1989) *Molecular Cloning: A Laboratory Manual* (Cold Spring Harbor, Laboratory Press, Plainview, N.Y.; Gelvin et al. Plant Molecular Biology Manual (1990); each incorporated herein in its entirety by reference.

| Table of Abbreviations | | |
|---|---|---|
| Abbr | Element Name | Reference |
| GZPRO | 27 kD gamma zein promoter | Reina, M., et al., Nucleic Acids Res. 18(21): 6426 (1990) |
| RFP | DsRed2 | Clontech Laboratories, Mountain View, Ca |
| OLE | Oleosin promoter | |
| IRNT | inverted repeat, no terminator | N/A |
| LTP2 PRO | barley LTP2 promoter | Kalla, R., et al., Plant Journal, 4: 849–860, 1994; |
| LEG1A PRO | legumin1 promoter | U.S. Pat. Pub. No. 2006/0130184 |
| ZM-40 PRO | *Zea mays*-40 promoter | U.S. Pat. No. 6,403,862 |
| EAP1 PRO | EAP1 promoter | U.S. Pat. No. 7,081,566 |
| LTP1 PRO | LTP1 promoter | U.S. Pat. App. No. 11/408,223 |

Construct PHP19991 (see SEQ ID NO:17 for insert sequence) was prepared to down-regulate the UXS 6 sequence. However, because of the high level of homology with UXS5 and UXS7, it was expected PHP19991 should inhibit expression of UXS 5, 6 and 7, but not UXS8. Maize was transformed with PHP19991 by *Agrobacterium*-mediated transformation as described herein. The genotypes of T1 kernels from the same event were screened with PCR, and the endosperms pooled into WT or transgenic. Hemicellulose analysis was performed with pooled endosperms as described herein.

PHP19991: GZ PRO:UXS6 IRNT:OLE PRO
Construct and sequence homology:
PHP19991/UXS6F vs UXS1=47.1%
PHP19991/UXS6F vs UXS2=48.2%
PHP19991/UXS6F vs UXS3=55.8%
PHP19991/UXS6F vs UXS4=57.3%
PHP19991/UXS6F vs UXS5=90.5%
PHP19991/UXS6F vs UXS6=100%
PHP19991/UXS6F vs UXS7=97.9%
PHP19991/UXS6F vs UXS8=65.9%

The effects of co-suppression using the PHP19991 cassette were to reduce the arabinoxylan contents in transgenic endosperm by up to about 20% in the T1 generation. The results demonstrate that UXS 5, 6, and/or 7 contribute part of the UDP-xylose substrate for hemicellulose synthesis.

Construct PHP21179 (see SEQ ID NO:18 for insert) was prepared to down-regulate the UXS2 sequence. Because of the high level of homology, PHP21179 was expected to inhibit expression of UXS 1 and 2 (Type A), the soluble isoforms of UXS in maize. Maize was transformed with PHP21179 by *Agrobacterium*-mediated transformation as described herein. The genotypes of T1 kernels from the same event were screened with PCR, and the endosperms pooled into WT or transgenic. Hemicellulose analysis was performed with pooled endosperms.

PHP21179:LEG1A PRO:Uxs2 IRNT ZM-40 PRO:Uxs2 (IRNT)
Construct and sequence homology:
PHP21179/UXS2F vs UXS1=94.2%
PHP21179/UXS2F vs UXS2=100%
PHP21179/UXS2F vs UXS3=65.7%
PHP21179/UXS2F vs UXS4=65.5%
PHP21179/UXS2F vs UXS5=66.2%
PHP21179/UXS2F vs UXS6=65.7%
PHP21179/UXS2F vs UXS7=66.1%
PHP21179/UXS2F vs UXS8=65.5%

The arabinoxylan contents in transgenic endosperm transformed with PHP21179 also showed up to about a 20% reduction in the T1 generation. The results show that UXS1 and 2 also play a role in producing UDP-xylose for hemicellulose synthesis.

Construct PHP21180 (ZM-40 PRO:Uxs2 IRNT::EAP1B PRO:Uxs2 IRNT) was prepared and transformed into maize by *Agrobacterium*-mediated transformation, as discussed above. T0 events of PHP21180 were selfed. Hence only 25% of the seeds would be expected to be wild-type in a segregating ear and 25% would be homozygous transgenic.

Twenty seeds from 12 events of PHP21180 were dissected to separate endosperm, embryo and pericarp. Twenty mg of ground endosperm was PCR genotyped to identify wild type and transgenic seeds using MOPAT primers. Nine out of the 12 events that segregated as single copy were further used for cell wall analysis. Embryo from seeds that segregated as wild type and transgenic seeds were pooled for each event. Four samples of 15-25 mg were used for cell wall sugar analysis. Reduction of arabinoxylan contents in transgenic embryos of up to 50% of control levels were observed.

Construct PHP21807 (see SEQ ID NO: 19 for insert sequence) was prepared to inhibit both Type A and Type C isoforms of UXS. Based on sequence comparisons, this construct was expected to down-regulate UXS 1, 2, 5, 6, 7, and possibly UXS 8. PHP21807 was transformed into maize by *Agrobacterium*-mediated transformation. The genotypes of T1 kernels from the same event were screened with PCR, and the endosperms pooled into WT or transgenic. Hemicellulose analysis was performed with pooled endosperms as described herein.

PHP21807:LEG1APRO:[Uxs2::Uxs6] IRNT ZM-40 PRO:[Uxs2::Uxs6] IRNT
Construct and sequence homology:
PHP21807/UXS2F vs UXS1=94.2%
PHP21807/UXS2F vs UXS2=100%
PHP21807/UXS2F vs UXS3=65.7%
PHP21807/UXS2F vs UXS4=65.5%
PHP21807/UXS2F vs UXS5=66.2%
PHP21807/UXS2F vs UXS6=65.7%
PHP21807/UXS2F vs UXS7=66.1%
PHP21807/UXS2F vs UXS8=65.5%
PHP21807/UXS6F vs UXS1=65.3%
PHP21807/UXS6F vs UXS2=66.2%
PHP21807/UXS6F vs UXS3=71.9%
PHP21807/UXS6F vs UXS4=72.0%
PHP21807/UXS6F vs UXS5=95.4%
PHP21807/UXS6F vs UXS6=100%
PHP21807/UXS6F vs UXS7=99.2%
PHP21807/UXS6F vs UXS8=85.6%

Transformation with PHP21807 resulted in a slightly greater reduction in arabinoxylan content in transgenic endosperm in the T1 generation, compared to either PHP19991 or PHP21179 alone, with up to about a 25% decrease observed.

Although the UXS sequences, enzyme activities, and cellular localizations have been studied in plant species other than maize, their involvement in hemicellulose biosynthesis has not previously been demonstrated. These results provide the first demonstration that inhibiting expression of UXS causes a reduction in plant hemicellulose accumulation. The results also demonstrate that both the soluble and membrane bound UXS play a role in producing UDP-xylose for hemicellulose synthesis.

Example 5

Additional Co-Suppression Studies of UDP-Xylose Synthases

T2 generation seeds were produced by back-crossing transgenic T1 plants. The presence of UXS nucleic acid sequences were determined by PCR analysis, using construct specific primers. Arabinoxylan content was determined in pooled samples as described in Example 3. Maize T2 endosperm transformed with PHP19991, PHP21179, and PHP21807 all showed reduced hemicellulose content, with a greater reduction in arabinoxylan content observed in the T2 endosperm compared to T1 endosperm.

PHP23388: LTP1 PRO:RFP::GZ PRO:UXS2-UXS6 IRNT: OLE PRO

A stacked construct containing sequences targeted against Type A and Type C isoforms was prepared and transformed into maize. T1 endosperm containing the construct were analyzed for hemicellulose, cellulose and hemicellulosic galactose content. Inhibition of two types of UXS isoforms resulted in a greater decrease in hemicellulose content than inhibition of Type A alone, or Type C alone.

This contruct contained a different promoter than PHP21807:LTP1, a pericarp preferred promoter. The insert sequence in PHP23388 was the same as in PHP21807. PHP23388 was transformed into maize by *Agrobacterium*-mediated transformation as described herein. Hemicellulose content of T1 endosperm was determined as described above.

Construct PHP23388 resulted in a greater inhibition of hemicellulose content than PHP21807 as well as an unexpected reduction in cellulose and hemicellulosic galactose. Hemicellulose was reduced up to 50% in both endosperm and embryo with the majority of events having reductions of 20% or more. Cellulose was reduced up to 25% in both embryo and endosperm with the majority of events having at least a 10% reduction in both tissues. Embryo galactose was reduced by at least 20% in the majority of events and endosperm galactose reduced by at least 10% in most events.

LTP2 PRO:RFP::GZ PRO: UXS2-UXS6-UXS3-UXS8 IRNT: OLE PRO

LTP2 PRO:RFP::GZ PRO: UXS3-UXS8 IRNT: OLE PRO

These constructs are transformed by *Agrobacterium* transformation into maize as described above. T1 seed are analyzed and compared to wild-type to determine the function of Type B UXS.

LTP1 PRO: UXS2-UXS6-UXS3-UXS8 IRNT

LTP1 PRO: ADH1 INTRON: UXS2-UXS6 IRNT

These constructs are transformed by *Agrobacterium* transformation into maize as described above. T1 seed are analyzed and compared to wild-type and other transformants to determine the efficacy and effects of UXS on pericarp to achieve greater reduction of fiber in seed.

Example 6

*Agrobacterium*-Mediated Transformation of Sorghum

For *Agrobacterium*-mediated transformation of sorghum the method of Cai et al. is employed (U.S. patent application Ser. No. 09/056,418), the contents of which are hereby incorporated by reference). This method can be employed with any of the nucleotide sequences described above.

Example 7

Transformation of Maize Embryos by Particle Bombardment

Immature maize embryos from greenhouse donor plants are bombarded with a plasmid containing any of the nucleotide sequences disclosed above, operably linked to a selected promoter, plus a plasmid containing the selectable marker gene PAT (Wohlleben et al. (1988) *Gene* 70:25-37) that confers resistance to the herbicide Bialaphos. Transformation is performed as follows.

Preparation of Target Tissue

The ears are surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid cassette comprising the nucleotide sequence of interest operably linked to a promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for the desired phenotypic trait.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 111117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 8

Transformation of Rice Embryogenic Callus by Bombardment

Embryogenic callus cultures derived from the scutellum of germinating seeds serve as the source material for transformation experiments. This material is generated by germinating sterile rice seeds on a callus initiation media (MS salts, Nitsch and Nitsch vitamins, 1.0 mg/l 2,4-D and 10 µM $AgNO_3$) in the dark at 27-28° C. Embryogenic callus proliferating from the scutellum of the embryos is then transferred to CM media (N6 salts, Nitsch and Nitsch vitamins, 1 mg/l 2,4-D, Chu et al., 1985, Sci. Sinica 18:659-668). Callus cultures are maintained on CM by routine sub-culture at two week intervals and used for transformation within 10 weeks of initiation.

Callus is prepared for transformation by subculturing 0.5-1.0 mm pieces approximately 1 mm apart, arranged in a circular area of about 4 cm in diameter, in the center of a circle of Whatman #541 paper placed on CM media. The plates with callus are incubated in the dark at 27-28 C for 3-5 days. Prior to bombardment, the filters with callus are transferred to CM supplemented with 0.25 M mannitol and 0.25 M sorbitol for 3 hr. in the dark. The petri dish lids are then left ajar for 20-45 minutes in a sterile hood to allow moisture on tissue to dissipate.

Circular plasmid DNA from two different plasmids, one containing the selectable marker for rice transformation and one containing a nucleic acid of interest, are co-precipitated onto the surface of gold particles. To accomplish this, a total of 10 µg of DNA at a 2:1 ratio of trait:selectable marker DNAs is added to a 50 µl aliquot of gold particles resuspended at a concentration of 60 mg/ml. Calcium chloride (50 µl of a 2.5 M solution) and spermidine (20 µl of a 0.1 M solution) are then added to the gold-DNA suspension as the tube is vortexing for 3 min. The gold particles are centrifuged in a microfuge for 1 sec and the supernatant removed. The gold particles are then washed twice with 1 ml of absolute ethanol and then resuspended in 50 µl of absolute ethanol and sonicated (bath sonicator) for one second to disperse the gold particles. The gold suspension is incubated at −70 C for five minutes and sonicated (bath sonicator) if needed to disperse the particles. Six µl of the DNA-coated gold particles are then loaded onto mylar macrocarrier disks and the ethanol is allowed to evaporate.

At the end of the drying period, a petri dish containing the tissue is placed in the chamber of the PDS-1000/He. The air in the chamber is then evacuated to a vacuum of 28-29 inches Hg. The macrocarrier is accelerated with a helium shock wave using a rupture membrane that bursts when the He pressure in the shock tube reaches 1080-1100 psi. The tissue is placed approximately 8 cm from the stopping screen and the callus is bombarded two times. Five to seven plates of tissue are bombarded in this way with the DNA-coated gold particles. Following bombardment, the callus tissue is transferred to CM media without supplemental sorbitol or mannitol.

Within 3-5 days after bombardment the callus tissue is transferred to SM media (CM medium containing 50 mg/l hygromycin). To accomplish this, callus tissue is transferred from plates to sterile 50 ml conical tubes and weighed. Molten top-agar at 40° C. is added using 2.5 ml of top agar/100 mg of callus. Callus clumps are broken into fragments of less than 2 mm diameter by repeated dispensing through a 10 ml pipet. Three ml aliquots of the callus suspension are plated onto fresh SM media and the plates incubated in the dark for 4 weeks at 27-28° C. After 4 weeks, transgenic callus events are identified, transferred to fresh SM plates and grown for an additional 2 weeks in the dark at 27-28° C.

Growing callus is transferred to RM1 media (MS salts, Nitsch and Nitsch vitamins, 2% sucrose, 3% sorbitol, 0.4% gelrite+50 ppm hyg B) for 2 weeks in the dark at 25° C. After 2 weeks the callus is transferred to RM2 media (MS salts, Nitsch and Nitsch vitamins, 3% sucrose, 0.4% gelrite+50 ppm hyg B) and placed under cool white light (~40 µEm$^{-2}$ s$^{-1}$) with a 12 hr photoperiod at 25° C. and 30-40% humidity. After 2-4 weeks in the light, callus generally begins to organize, and form shoots. Shoots are removed from surrounding callus/media and gently transferred to RM3 media (½×MS salts, Nitsch and Nitsch vitamins, 1% sucrose+50 ppm hygromycin B) in phytatrays (Sigma Chemical Co., St. Louis, Mo.) and incubation is continued using the same conditions as described in the previous step.

Plants are transferred from RM3 to 4" pots containing Metro mix 350 after 2-3 weeks, when sufficient root and shoot growth has occurred. Plants are grown using a 12 hr/12 hr light/dark cycle using ~30/18° C. day/night temperature regimen.

Example 9

Transformation of Dicots

A seed-specific expression cassette composed of the promoter and transcription terminator from the gene encoding the β subunit of the seed storage polypeptide phaseolin from the bean *Phaseolus vulgaris* (Doyle et al. (1986) *J. Biol. Chem.* 261:9228-9238) can be used for expression of nucleic acids in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), SmaI, KpnI and XbaI. The entire cassette is flanked by Hind III sites.

The cDNA fragment of this gene can be generated by polymerase chain reaction (PCR) of the cDNA clone using appropriate oligonucleotide primers. Cloning sites can be incorporated into the oligonucleotides to provide proper orientation of the DNA fragment when inserted into the expression cassette. Amplification is then performed and the isolated fragment is inserted into a pUC18 cassette carrying the seed expression cassette.

Soybean embryos can then be transformed with the expression cassette comprising nucleic acid sequences as disclosed herein. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures can then be transformed by the method of particle gun bombardment (Klein et al. (1987) *Nature* (London) 327:70-73, U.S. Pat. No. 4,945,050). A DuPont Biolistic PDS1000/HE instrument (helium retrofit) can be used for these transformations.

A selectable marker gene which can be used to facilitate soybean transformation is a nucleic acid composed of the 35S promoter from Cauliflower Mosaic Virus (Odell et al.(1985) *Nature* 313:810-812), the hygromycin phosphotransferase gene from plasmid pJR225 (from *E. coli*; Gritz et al.(1983) *Gene* 25:179-188) and the 3' region of the nopaline synthase gene from the T-DNA of the Ti plasmid of *Agrobacterium tumefaciens*. The seed expression cassette comprising the phaseolin 5' region, a nucleic acid insert of interest and the phaseolin 3' region can be isolated as a restriction fragment. This fragment can then be inserted into a unique restriction site of the cassette carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media can be exchanged with fresh media, and eleven to twelve days post bombardment with fresh media containing 50 mg/mL hygromycin. This selective media can be refreshed weekly. Seven to eight weeks post bombardment, green, transformed tissue can be observed growing from untransformed, necrotic embryogenic clusters. Isolated green tissue is removed and inoculated into individual flasks to generate new, clonally propagated, transformed embryogenic suspension cultures. Each new line can be treated as an independent transformation event. These suspensions can then be subcultured and maintained as clusters of immature embryos or regenerated into whole plants by maturation and germination of individual somatic embryos.

Example 10

Expression of a Nucleic acid in Microbial Cells

The cDNAs encoding the instant polypeptides can be inserted into the T7 *E. coli* expression cassette pBT430. This cassette is a derivative of pET-3a (Rosenberg et al. (1987) *Gene* 56:125-135) which employs the bacteriophage T7 RNA polymerase/T7 promoter system. Plasmid pBT430 is constructed by first destroying the EcoR I and Hind III sites in pET-3a at their original positions. An oligonucleotide adaptor containing EcoR I and Hind III sites is inserted at the BamH I site of pET-3a. This created pET-3aM with additional unique cloning sites for insertion of genes into the expression cassette. Then, the Nde I site at the position of translation initiation is converted to an Nco I site using oligonucleotide-directed mutagenesis. The DNA sequence of pET-3aM in this region, 5'-CATATGG, is converted to 5'-CCCATGG in pBT430.

Plasmid DNA containing a cDNA can be appropriately digested to release a nucleic acid fragment encoding the polypeptide. This fragment can then be purified on a 1% NuSieve GTG low melting agarose gel (FMC). Buffer and agarose contain 10 μg/ml ethidium bromide for visualization of the DNA fragment. The fragment can then be purified from the agarose gel by digestion with GELase (Epicentre Technologies) according to the manufacturer's instructions, ethanol precipitated, dried and resuspended in 20 μL of water. Appropriate oligonucleotide adapters can be ligated to the fragment using T4 DNA ligase (New England Biolabs, Beverly, Mass.). The fragment containing the ligated adapters can be purified from the excess adapters using low melting agarose as described above. The cassette pBT430 is digested, dephosphorylated with alkaline phosphatase (NEB) and deproteinized with phenol/chloroform as described above. The prepared cassette pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-p-galactoside, the inducer) can be added to a final concentration of 0.4 mM and incubation can be continued for 3 h at 250. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the polypeptide concentration of the supernatant determined. One microgram of polypeptide from the soluble fraction of the culture can be separated by SDS-polyacrylamide gel electrophoresis. Gels can be observed for polypeptide bands migrating at the expected molecular weight.

Example 11

Preparation of Transgenic Sunflowers

Biolistics/Bombardment

Mature sunflower seeds are dehulled and surface sterilized for 30 min in a 20 percent Chlorox® bleach solution with the addition of two drops of Tween 20 per 50 ml of solution. Seeds are rinsed twice with distilled water.

Seeds are imbibed in distilled water for 60 min following the surface sterilization procedure. The cotyledons of each seed are broken off to produce a clean fracture at the plane of the embryonic axis. Following excision of the root tip, the explants are bisected longitudinally between the primordial leaves. The two halves are placed cut surface up on GBA medium consisting of Murashige and Skoog mineral elements, Shepard's vitamin additions, 40 mg/l adenine sulfate, 30 g/l sucrose, 0.5 mg/l 6-benzyl-aminopurine, 0.25 mg/l indole-3-acetic acid, 0.1 mg/l gibberellic acid pH 5.6, and 8 g/l Phytagar.

Thirty to forty explants at a time are placed in a circle at the center of a 60×20 mm plate for microprojectile bombardment. Approximately 4.7 mg of 1.8 um tungsten microprojectiles are re-suspended in 25 ml of sterile TE buffer (10 mM Tris-Cl, 1 mM EDTA pH 8) and 1.5 m aliquots are used per bombardment. Each plate is bombarded twice through a 150 um Nytex screen placed 2 cm above the samples in a PDS 1000® particle acceleration device.

Agro Transformation

Plasmid is introduced into *Agrobacterium tumefaciens* via freeze thawing as described by Holsters et al., Mol. Gen. Genet. 163: 181-7 (1978). Bacteria used for transformation are grown overnight (28° C. and 100 RPM continuous agitation) in liquid YEP medium (10 g/l yeast extract, 10 g/l Bactopeptone and 5 g/l NaCl, pH 7.0) in the presence of kanamycin. The suspension is used when it reached an OD600 of 0.5 in an incubation medium comprised of 12.5 mM 2-(N-morpholino)ethanesulfonic acid, MES, 1 g/l NH4Cl and 0.3 g/l MgSO4 at pH 5.7.

Freshly bombarded explants are placed in an *Agrobacterium* suspension, mixed and left undisturbed for 30 min. The explants are then transferred to GBA medium with co-cultivated cut surfaces down at 26° C. for 18-h days. After 3 days of co-cultivation, the explants are transferred to 374B media (GBA medium lacking growth regulators and having a reduced sucrose level of 1 percent) supplemented with 250 mg/l cefotaxime and 25, 50, 100 or 200 mg/l kanamycin sulfate. The explants are cultured for 2-5 weeks on the supplemented medium and then transferred to fresh 374B medium lacking kanamycin for 1-2 weeks of continued development. Explants with differentiating, antibiotic resistant areas of growth that had not produced shoots suitable for excision are transferred to GBA medium containing 250 mg/l cefotaxime for a second 3-day phytohormone treatment. Leaf samples from green, kanamycin-resistant shoots are assayed for the presence of selectable marker activity. Those shoots that fail to exhibit activity are discarded.

Marker positive shoots are grafted to Pioneer® hybrid in vitro-grown sunflower seedling rootstock. Surface sterilized seeds are germinated in 48-0 medium (half strength Murashige and Skoog salts, 0.5 percent sucrose, 0.3 percent gelrite pH 5.6) and grown under the conditions described for explant culture. The upper portion of each seedling is removed, a 1-cm vertical slice is made in each hypocotyl, and each transformed shoot is inserted into a cut. The entire area of each prepared graft is wrapped with parafilm to secure each shoot. Grafted plants are transferred to soil following 1 week of in vitro culture. Grafts in soil are maintained under high humidity conditions, followed by a slow acclimatization to a greenhouse environment.

Transformed sectors of T0 plants (parental generation) maturing in the greenhouse are identified by marker analysis of leaf extracts while transgenic seeds harvested from marker-positive T0 plants are identified by analysis of small portions of dry seed cotyledon. Leaf and seed assays of confirmed transgenics also are performed for segregation analysis of selfed progeny populations. Transgenic seeds from a number of events are cultivated under field conditions. The transgenics are grown in an isolation cage designed to minimize pollen dissemination by foraging insects.

DNA is isolated from immature leaves of greenhouse grown sunflower plants by a urea buffer extraction protocol. For each sample, leaf tissue (2 g) is frozen in liquid nitrogen, ground with a mortar and pestle, and mixed into 6 ml of urea extraction buffer (50 mM TRIS-HCl pH 8.0, 7M urea, 0.31 M NaCl, 1 percent sarcosine). An equal volume of phenol:chloroform (1:1) is added and the mixture is shaken at room temperature for 15 minutes. After centrifugation (12,000×g, 15 min) the clarified supernatant is removed. DNA is precipitated by the addition of 1 ml of 4.4 M ammonium acetate (pH 5.2) and 7 ml isopropanol. The DNA is collected with a Pasteur pipette hook, allowed to dry for 15 minutes, and then resuspended in 0.5 M TE buffer as described in Ausubel et al., CURRENT PROTOCOLS IN MOLECULAR BIOLOGY, (1989). DNA (about 10 mg) is digested twice with 5-10 units of Xbal/mg DNA at 370 for 3 hours. Samples are subjected to electrophoresis on a one percent agarose gel and transferred onto nylon membranes for hybridization analysis as described by Southern, J. Mol. Biol. 98: 503-17 (1975).

Appropriate enzyme restriction digestion linearizes the binary plasmid. T-DNA junctions with plant genomic DNA at the right border are detected using restriction enzyme digestion followed by hybridization to a radiolabeled probe generated by random prime labeling of the marker fragment as described by Feinberg & Vogelstein, Anal. Biochem. 137: 266-7 (1984).

REFERENCES

Bar-Peled M, Griffith C L, Doering T L (2001) Functional cloning and characterization of a UDPglucuronic acid decarboxylase: the pathogenic fungus *Cryptococcus neoformans* elucidates UDP-xylose synthesis. Proc Natl Acad Sci USA 98:12003-12008

Gu X, Bar-Peled M (2004) The biosynthesis of UDP-galacturonic acid in plants: functional cloning and characterization of *Arabidopsis* UDP-D-galacturonic acid 4-epimerase. Plant Physiol 136:4256-4264

Harper A D, Bar-Peled M (2002) Biosynthesis of UDP-Xylose. Cloning and characterization of a novel *Arabidopsis* gene family, UXS, encoding soluble and putative membrane-bound UDP-Glucuronic acid decarboxylase isoforms. Plant Physiol 130:2188-2198

Hayashi T, Koyama T, Matsuda K (1988) Formation of UDP-xylose and xyloglucan in soybean Golgi membranes. Plant Physiol 87:341-345

Kobayashi M, Nakagawa H, Suda I, Miyagawa I, Matoh T (2002) Purification and cDNA cloning of UDP-D-glucuronate carboxy-lyase (UDP-D-xylose synthase) from pea seedlings. Plant Cell Physiol 43:1259-1265

Moriarity J L, Hurt K J, Resnick A C, Storm P B, Laroy W, Schnaar R L, Snyder H (2002) UDP-glucoronate decarboxylase, a key enzyme in proteoglycan synthesis. J Biol Chem 277:16968-16975

Pagny S, Bouissonnie F, Sarkar M, Follet-Gueye M L, Driouich A, Schachter H, Faye L, Gomord V (2003) Structural requirements for *Arabidopsis* beta 1,2-xylosyltransferase activity and targeting to the Golgi. Plant J 33:189-203

Pattathil S, Harper A D, Bar-Peled M (2005) Biosynthesis of UDP-xylose: characterization of membrane-bound AtUxs2. Planta. January 18

Reiter W D, Vanzin G F (2001) Molecular genetics of nucleotide sugar interconversion pathways in plants. Plant Mol Biol 47:95-113

Seifert G J (2004) Nucleotide sugar interconversion and cell wall biosynthesis: how to bring the inside to outside. Curr Opin Plant Biol 7:277-284

Suzuki K, Suzuki Y, Kitamura S (2003) Cloning and expression of a UDP-glucuronic acid decarboxylase gene in rice. J Exp Bot 54:1997-1999

Wheatley E R, Davies D R, Bolwell G P (2002) Characterisation and immunolocation of an 87 kDa polypeptide associated with UDP-glucuronic acid decarboxylase activity from differentiating tobacco cells (*Nicotiana tabacum* L.). Phytochemistry 61:771-780

What is claimed is:

1. An isolated polynucleotide comprising a polynucleotide that is the complement of SEQ ID NO:3 wherein the isolated polynucleotide reduces the level of arabinoxylan.

2. An expression cassette comprising the polynucleotide of claim 1 operably linked to a seed preferred promoter.

3. The expression cassette of claim 2 further comprising any combination of additional polynucleotide sequences of interest.

4. A plant cell containing the polynucleotide of claim 1.

5. A transformed plant comprising the polynucleotide of claim 1.

6. The transformed plant of claim 5, wherein the plant is corn, barley, soybean, sorghum, wheat, rice, alfalfa, safflower, sunflower, canola, cotton, or millet.

7. A transformed seed from the transformed plant of claim 5.

8. A method for reducing arabinoxylan levels in a plant cell, comprising:
   (a) transforming the host cell with the polynucleotide of claim 1; and
   (b) growing the transformed host cell to reduce arabinoxylan levels in the plant cell.

9. The method of claim 8, further comprising transforming the plant cell with any combination of additional polynucleotide sequences of interest.

10. The method of claim 8, further comprising producing a transformed plant from the plant cell.

* * * * *